US012049637B2

(12) United States Patent
Panevska et al.

(10) Patent No.: US 12,049,637 B2
(45) Date of Patent: Jul. 30, 2024

(54) BIO-PESTICIDES FOR CONTROLLING PLANT PESTS

(71) Applicants: KMETIJSKI INŠTITUT SLOVENIJE, Ljubljana (SI); Univerza v Ljubljani, Ljubljana (SI)

(72) Inventors: Anastasija Panevska, Sofija (BG); Jaka Razinger, Ljubljana (SI); Kristina Sepčić, Ljubljana (SI); Peter Maček, Brezovica (SI); Matej Skočaj, Materija (SI); Špela Modic, Ljubljana (SI); Maruša Novak, Krško (SI); Matej Butala, Ljubljana (SI); Vesna Hodnik, Žabnica (SI); Maja Grundner, Ljubljana (SI); Tom Turk, Ljubljana-Šmartno (SI)

(73) Assignees: KMETIJSKI INSTITUT SLOVENIJE, Ljubljana (SI); Univerza v Ljubljani, Ljubljana (SI)

( * ) Notice: Subject to any disclaimer, the term of this patent is extended or adjusted under 35 U.S.C. 154(b) by 410 days.

(21) Appl. No.: 16/649,385

(22) PCT Filed: Sep. 29, 2017

(86) PCT No.: PCT/EP2017/074877
§ 371 (c)(1),
(2) Date: Mar. 20, 2020

(87) PCT Pub. No.: WO2019/063101
PCT Pub. Date: Apr. 4, 2019

(65) Prior Publication Data
US 2020/0245628 A1    Aug. 6, 2020

(51) Int. Cl.
*A01N 63/50* (2020.01)
*C07K 14/375* (2006.01)
*C12N 15/82* (2006.01)

(52) U.S. Cl.
CPC ......... *C12N 15/8286* (2013.01); *A01N 63/50* (2020.01); *C07K 14/375* (2013.01)

(58) Field of Classification Search
None
See application file for complete search history.

(56) References Cited

U.S. PATENT DOCUMENTS 7,323,556 B2 * 1/2008 Bing .................... C12Q 1/6876
536/23.1

OTHER PUBLICATIONS

Centre for Advanced Molecular Imaging (2015, https://imagingcoe.org/carnivorous-mushrooms-reveal-human-immune-trick/).*
Lukoyanova et al (2015, PLoS Biol 13(2): e1002049. doi:10.1371/journal.pbio.1002049).*
Sakurai et al.A (2008, GenBank BAD66666).*
Sakurai et al.B (2008, GenBank BAD66669).*
Bhat et al.(2013, J. Lipid Res. 54:2933-2943).*
Ota et al.(2013, Biochimie 95:1855-1864, including supplemental material).*
Ferrari et al (2008, Plant Physiol. 146:669-681).*
Lorito et al (1998, PNAS 95:7860-7865).*
Martinez et al (2015, Planta 242:39-52).*
Desai et al (2010, Biotechnol. Adv. 28 427-435).*
Alyokhin, A., et al., "Colorado Potato Beetle Resistance to Insecticides," 2008, American Journal Of Potato Research, 85(6), 395-413. http://dx.doi.org/10.1007/s12230-008-9052-0.
Alyokhin, A., et al., "The Red Queen in a potato field: integrated pest management versus chemical dependency in Colorado potato beetle control," 2014, Pest Management Science, 71(3), 343-356. http://dx.doi.org/10.1002/ps.3826.
Berne, S., "Aegerolysins: Structure, function, and putative biological role," 2009, Protein Science, 18(4), 694-706. http:/dx.doi.org/10.1002/pro.85.
Butala et al., "Aegerolysins: Lipid-binding proteins with versatile functions. Seminars In Cell And Developmental Biology," http://dx.doi.org/10.1016/j.semcdb.2017.05.002.
Casagrande, Ra. (1987). "The Colorado Potato Beetle: 125 Years of Mismanagement," American Entomologist, 33 (3), 142-150. https://doi.org/10.1093/besa/33.3.142.
Chu et al., "Differential effects of RNAi treatments on field populations of the western corn rootworm," 2014, Pesticide Biochemistry And Physiology, 110, 1-6. http:/dx.doi.org/10.1016/j.pestbp.2014.02.003.
Crone et al., "The phospholipids of the housefly, *Musca domestica*," 1963. Biochemical Journal, 89, 11-21.
Devine et al., "Insecticide use: Contexts and ecological consequences," 2007. Agriculture And Human Values, 24 (3), 281-306. http://dx.doi.org/10.1007/s10460-007-9067-z.
Gassman, A, "Field-evolved resistance to Bt maize by western corn rootworm: Predictions from the laboratory and effects in the field," 2012, Journal Of Invertebrate Pathology, 110(3), 287-293. http://dx.doi.org/10.1016/j.ip.2012.04.006.
Gassman et al., "Field-Evolved Resistance to Bt Maize by Western Corn Rootworm," 2011, Plos One, 6(7), e22629. http://dx.doi.org/10.1371/journal.pone.0022629.

(Continued)

*Primary Examiner* — Anne Kubelik
(74) *Attorney, Agent, or Firm* — Renner, Otto, Boisselle & Sklar, LLP

(57) ABSTRACT

The present invention relates to cytolytic bi-component protein complexes consisting of a plurality of molecules of a member of the aegerolysin family and a plurality of molecules of a member of the MACPF superfamily, and particularly to their use for controlling a plant pest, such as for controlling Colorado potato beetle (*Leptinotarsa decemlineata*) or Western corn rootworm (*Diabrotica virgifera virgifera*). More specifically, the invention relates to cytolytic bi-component protein complexes formed by a plurality of molecules of one of the aegerolysins ostreolysin A6 (OlyA6), pleurotolysin A2 (PlyA2) and erylysin A (EryA) with a plurality of molecules of pleurotolysin B (PlyB) or similar proteins, which have been shown to be toxic for the aforementioned agricultural pest insects.

21 Claims, 8 Drawing Sheets

Specification includes a Sequence Listing.

(56) References Cited

OTHER PUBLICATIONS

Jakka, S, et al., "Broad-spectrum resistance to Bacillus thuringiensis toxins by western corn rootworm (*Diabrotica virgifera virgifera*," 2016, Scientific Reports, 6(1). http://dx.doi.org/10.1038/srep27860.
Kaiser-Alexnat, R. "Protease activities in the midgut of Western corn rootworm (*Diabrotica virgifera* LeConte)," 2009, Journal Of Invertebrate Pathology, 100(3), 169-174. http://dx.doi.org/10.1016/j.jip.2009.01.003.
Kelker et al., "Structural and Biophysical Characterization of Bacillus thuringiensis Insecticidal Proteins Cry34Ab1 and Cry35Ab1," 2014, Plos One, 9(11), e112555. http:/dx.doi.org/10.1371/journal.pone.0112555.
Kuhlmann et al., "Possibilities for biologicalcontrol of the western corn rootworm, *Diabrotica virgiferavirgifera* LeConte, in Central Europe," 1998, Biocontrol News And Information, 19, 59-68.
Lukoyanova et al., "Conformational changes during pore formation by the perforin-related protein pleurotolysin," 2015, PLos Biology, 13 (2), 1-15. http://dx.doi.org/10.1371/journal.pbio.1002049.
Masson et al., "A NovelBacillus thuringiensis (PS149B1) Containing a Cry34Ab1/Cry35Ab1 Binary Toxin Specific for the Western Corn Rootworm*Diabrotica virgifera virgifera*LeConte Forms Ion Channels in Lipid Membranes," 2004, Biochemistry, 43(38), 12349-12357. http://dx.doi.org/10.1021/bi048946z.
Meinke et al., "Adult Susceptibility of Nebraska Western Corn Rootworm (Coleoptera: Chrysomelidae) Populations to Selected Insecticides," 1998, Journal of Economic Entomology, 91(3), 594-600.
Meissle et al., "Susceptibility of Diabrotica virgifera (Coleoptera: Chrysomelidae) to the Entomopathogenic Fungus *Metarhizium anisopliae* when Feeding on Bacillus thuringiensis Cry3Bb1-Expressing Maize," 2009, Applied And Environmental Microbiology, 75(12), 3937-3943. http://dx.doi.org/10.1128/aem.00432-09.
Ota et al., "Membrane cholesterol and sphingomyelin, and ostreolysin A are obligatory for pore-formation by a MACPF/CDC-like pore-forming protein, pleurotolysin B," 2013, . Biochimie, 95(10), 1855-1864. http://dx.doi.org/10.1016/j.biochi.2013.06.012.
Ota et al., "Fungal MACPF-Like proteins and Aegerolysins: Bicomponent pore-forming proteins?," 2014, Subcellular Biochemistry, 80, 271-91.
Pereira et al., "Evidence of Field-Evolved Resistance to Bifenthrin in Western Corn Rootworm (*Diabrotica virgifera virgifera* LeConte) Populations in Western Nebraska and Kansas," 2015, PlosS One, 10(11), e0142299. http://dx.doi.org/10.1371/journal.pone.0142299.
Perlak et al., "Genetically improved potatoes: protection from damage by Colorado potato beetles," 1993, Plant Molecular Biology, 22(2), 313-321.
Qureshi et al., "The Cry Toxin Operon of *Clostridium bifermentans* subsp. *malaysia* Is Highly Toxic to Aedes Larval Mosquitoes," 2014, Applied And Environmental Microbiology, 80(18), 5689-5697. http://dx.doi.org/10.1128/aem.01139-14.
Sambrook et al., "Molecular cloning: A Laboratory Manual. Second edition," 1989, New York: Cold Spring Harbor Laboratory Press.
Sepčić et al., "Ostreolysin, a pore-forming protein from the oyster mushroom, interacts specifically with membrane cholesterol-rich lipid domains," 2004, FEBS Letters, 575(1-3), 81-85. http://dx.doi.org/10.1016/j.febslet.2004.07.093.
Shibata et al., "Isolation and characterization of a novel two-component hemolysin, erylysin A and B, from an edible mushroom, *Pleurotus eryngii*," Toxicon, 56(8), 1436-1442. http://dx.doi.org/10.1016/j.toxicon.2010.08.010.
Skočaj et al., "Tracking Cholesterol/Sphingomyelin-Rich Membrane Domains with the Ostreolysin A-mCherry Protein," 2014, Plos One, 9(3), e92783. http://dx.doi.org/10.1371/journal.pone.0092783.
Tomita et al., "Pleurotolysin, a Novel Sphingomyelin-specific Two-component Cytolysin from the Edible Mushroom*Pleurotus ostreatus*, Assembles into a Transmembrane Pore Complex," 2004, Journal Of Biological Chemistry, 279(26), 26975-26982. http://dx.doi.org/10.1074/jbc.m402676200.
Tu et al., "Field performance of transgenic elite commercial hybrid rice expressing Bacillus thuringiensis δ-endotoxin," 2000, Nature, 18, 1101-1104. http://dx.doi.org/10.1038/80310.
Vacaru et al., "Ceramide Phosphoethanolamine Biosynthesis in *Drosophila* Is Mediated by a Unique Ethanolamine phosphotransferase in the Golgi Lumen," 2013, The Journal of Biological Chemistry, 288(16), 11520-30.
Yalpani et al, "An Alcaligenes strain emulates Bacillus thuringiensis producing a binary protein that kills corn rootworm through a mechanism similar to Cry34Ab1/Cry35Ab1," 2017, Scientific Reports, 7(1). http://dx.doi.org/10.1038/s41598-017-03544-9.
Zhang et al., "The protein P23 identifies capsule-forming plasmatocytes in the moth *Pseudoplusia includens*," Elsevier, 2011, Developmental and Comparative Immunology, doi:10.1016/j.dci.2010.12.006.
Berne et al., "Pleurotus and Agrocybe hemolysins, new proteins hypothetically involved in fungal fruiting," 2002, Elsevier, Biochimica et Biophysica Acta 1570 (2002) 153-159.
Berne et al., "Effect of pH on the Pore Forming Activity and Conformational Stability of Ostreolysin, a Lipid Raft- Binding Protein from the Edible Mushroom," 2005, Biochemistry 2005, 44, 11137-11147.
Bhat et al., "Binding of a pleurotolysin ortholog from Pleurotus eryngii to sphingomyelin and cholesterol-rich membrane domains," Journal of Lipid Research vol. 54, 2013, pp. 2933-2943.
Chowdhury et al., "Lysophospholipids prevent binding of a cytolytic protein ostreolysin to cholesterol-enriched membrane domains," Elsevier, Toxicon 51 (2008) 1345-1356.
Kurahashi et al., "Homologous genes, Pe.pleurotolysin A and Pe.ostreolysin, are both specifically and highly expressed in primordia and young fruiting bodies of Pleurotus eryngii," 2013, Elsevier, mycoscience xxx (2013) 1-5, Mycoscience (2013), http://dx.doi.org/ 10.1016/j.myc.2013.06.005.
Juntes et al., "Ostreolysin induces sustained contraction of porcine coronary arteries and endothelial dysfunction in middle- and large-sized vessels," Elsevier, Toxicon (2009), doi:10.1016/j.toxicon.2009.06.005.
Lokar et al., "The role of cholesterol-sphingomyelin membrane nanodomains in the stability of intercellular membrane nanotubes," International Journal of Nanomedicine, 2012:7 1891-1902.
Maličev et al.,"Effect of ostreolysin, an Asp-hemolysin isoform, on human chondrocytes and osteoblasts, and possible role of Asp-hemolysin in pathogenesis" Medical Mycology Mar. 2007, 45, 123-130.
Nimri et al., "A recombinant fungal compound induces antiproliferative and pro-apoptotic effects on colon cancer cells," 2017, Oncotarget, www.impactjournals.com/oncotarget/, pp. 1-11.
Novak et al., "Fungal aegerolysin-like proteins:distribution, activities, and applications," 2015, Applied Microbiology and Biotechnology, ISSN 0175-7598 , vol. 99, No. 2, Appl Microbiol Biotechnol (2015) 99:601-610 DOI 10.1007/s00253-014-6239-9.
Reboji et al., "Ostreolysin, a Cytolytic Protein from Culinary-Medicinal Oyster Mushroom *Pleurotus ostreatus* (Jacq • Fr.) P. Kumm (Agaricomycetideae), and Its Potential Use in Medicine and Biotechnology," 2008 by Begell House Inc.
Anonymous : "Applications of aegerolysinlike proteins for detection and eradication of pests" by Jaka Razinger Research Project on ResearchGate, Sep. 30, 2016 (Sep. 30, 2016), XP55429246, Retrieved from the Internet: URL:https://www.researchgate.net/project/Applications-of-aegerolysinlike-proteins-for detection-and-eradication-of-pests [retrieved on Nov. 27, 2017] the whole document.
Reboul et al: "Giant MACPF/CDC pore forming toxins: A class of their own", Biochimica Et Biophysica Acta (BBA)-Biomembranes, Elsevier, Amsterdam, NL, vol. 1858, No. 3, Nov. 26, 2015 (Nov. 26, 2015), pp. 475-486, XP029402251, ISSN: 0005-2736, DOI:10.1016/J.BBAMEM.2015.11.017abstract p. 481, col. 1, paragraph 4—p. 482, col. 1, paragraph 1 figure 3 table 1.
Novak et al: "Fungal aegerolysin-like proteins: distribution, activities, and applications", Applied Microbiology and Biotechnology, Springer, Springer, DE, vol. 99, No. 2, Dec. 6, 2014 (Dec. 6, 2014), pp. 601-610, XP036127145, ISSN: 0175-7598, DOI: 10.1007/S00253-014-6239-9 retrieved on Dec. 6, 2014] abstract p. 601, paragraph 1—p. 604, paragraph 1.

(56) References Cited

OTHER PUBLICATIONS

Butala et al., "Aegerolysins: Lipid-binding proteins with versatile functions", Seminars In Cell and Developmental Biology., May 1, 2017 (May 1, 2017), XP55429293, GB ISSN: 1084-9521, DOI: 10.1016/j.semcdb.2017.05.002 the whole document.
International Search Report and Written Opinion for Corresponding International Application No. PCT/EP2017/074877 dated Dec. 8, 2017.
Rebojl et al., "Steroid structural requirements for interaction of ostreolysin, a lipid-raft binding cytolysin, with lipid monolayers and bilayers," Elsevier, Biochimica et Biophysica Acta 1758 (2006) 1662-1670.
Rebojl et al., "Ostreolysin affects rat aorta ring tension and endothelial cell viability in vitro," Elsevier, Toxicon 49 (2007) 1211-1213.
Rebojl et al., "EPR and FTIR studies reveal the importance of highly ordered sterol-enriched membrane domains for ostreolysin activity," Elsevier, Biochimica et Biophysica Acta 1798 (2010) 891-902.
Resnick et al., "Desmosome Assembly and Cell-Cell Adhesion Are Membrane Raft-dependent Processes," The Journal of Biological Chemistry vol. 286, No. 2, pp. 1499-1507, Jan. 14, 2011.
Resnick et al. "Highly Selective Anti-Cancer Activity of Cholesterol-Interacting Agents Methyl-β-Cyclodextrin and Ostreolysin A/Pleurotolysin B Protein Complex on Urothelial Cancer Cells," Plos One | DOI:10.1371/journal.pone.0137878 Sep. 11, 2015, pp. 1-19.
Sakurai et al., "Cloning, expression, and pore-forming properties of mature and precursor forms of pleurotolysin, a sphingomyelin-specific two-component cytolysin from the edible mushroom *Pleurotus ostreatus*," Biochimica et Biophysica Acta 1679 (2004) 65-73.
Schlumberger, "Permeability characteristics of cell-membrane pores inducedby ostreolysin A/pleurotolysin B, binary pore-forming proteins from the oyster mushroom," Elsevier, FEBS Letters 588 (2014) 35-40.
Sepčić et al. "Interaction of ostreolysin, a cytolytic protein from the edible mushroom *Pleurotus ostreatus*, with lipid membranes and modulation by lysophospholipids," Eur. J. Biochem. 270,1199-1210 (2003) FEBS 2003, doi: 10.1046/i.1432-1033.2003.03480.x.
Skočaj et al., "The Sensing of Membrane Microdomains Based on Pore-Forming Toxins," Current Medicinal Chemistry, 2013, 20, 491-50.
Skočaj et al., "Characterisation of plasmalemmal shedding of vesicles induced by the cholesterol/ sphingomyelin binding protein, ostreolysin A-mCherry," BBA—Biomembranes (2016), doi:10.1016/j.bbamem.2016.08.015.
Vezočnik et al., "Size fractionation and size characterization of nanoemulsions of lipid droplets and large unilamellar lipid vesicles by asymmetric-flow field-flow fractionation/multi-angle light scattering and dynamic light scattering," Elsevier, Journal of Chromatography A, 1418 (2015) 185-191.
Vidic et al., "Temporal and spatial expression of ostreolysin during development of the oyster mushroom (*Pleurotus ostreatus*)," Mycol. Res. 109 (3): 377-382 (Mar. 2005). f The British Mycological Society doi:10.1017/S0953756204002187 Printed in the United Kingdom.
Vrecl et al., "Effect of the ostreolysin A/pleurotolysin B pore-forming complex on intracellular Ca2+ activity in the vascular smooth muscle cell line A10," Elsevier, Toxicology in Vitro 29 (2015) 2015-2021.
Yamaji-Hasegawa et al., "Pore-forming toxins: Properties, diversity, and uses as tools to image sphingomyelin and ceramide phosphoethanolamine," Biochim. Biophys. Acta (2015), http://dx.doi.org/10.1016/j.bbamem.2015.10.012.
Zidar et al., "Liquid-Ordered Phase Formation in Cholesterol/Sphingomyelin Bilayers: All-Atom Molecular Dynamics Simulations," J. Phys. Chem. B 2009, 113, 15795-15802.
Zuzek et al., "Toxic and lethal effects of ostreolysin, a cytolytic protein from edible oyster mushroom (*Pleurotus ostreatus*), in rodents," Elsevier, Toxicon 48 (2006) 264-271.

Sepčić et al.; Cytolytic and Toxic Effects of Ostreolysin, a Protein from the Oyster Mushroom (*Pleurotus ostreatus*); 2009; Comp. Bio. Nat. Pro. vol. 2—Efficacy, Safety & Clinical Evaluation (Pt-1).
Nayak et al.; Characterization of recombinant terrelysin, a hemolysin of Aspergillus terreus; 2011; Mycopathologia; vol. 171.
Anderluh et al.; MACPF/CDC Proteins—Agents of Defence, Attack and Invasion; Subcellular Biochemistry; 2014; vol. 80.
Bhat et al.; Evaluation of aegerolysins as novel tools to detect and visualize ceramide phosphoethanolamine, a major sphingolipid in invertebrates; Jun. 9, 2015; The FASEB Journal; vol. 29; pp. 1-15.
Itasaka et al.; Occurence of Ceramide Phosphorylethanolamine Containing Hydroxy Fatty Acid in a Bivalve; 1973; Journal of Biochemistry; vol. 73; pp. 191-193.
Ludwick et al.; Minnesota field population of western corn rootworm (Coleoptera: Chrysomelidae) shows incomplete resistance to Cry34Ab1/Cry35Ab1 and Cry3Bb1; published 2017; Journal Of Applied Entomology; vol. 141; pp. 28-40.
Roberts et al.; Differential gene expression in Alternaria gaisen exposed to dark and light; published online Apr. 13, 2011; Mycol Progress.
Anderluh et al.; Pore Forming Toxins as useful Tools in Studies of Lipid Membrane Organization; published 2005; Proc. Indian Natl. Sci. Acad.; Part B, Biological Sciences 71; pp. 73-81.
Ngai et al.; A hemolysin from the mushroom *Pleurotus eryngii*; published 2006; Appl Microbiol Biotechnol; Biotechnologically Relevant Enzymes and Protein.
N. Lukoyanova et al.; Structure of membrane binding protein pleurotolysin B from Pleurotus ostreatus; Protein Data Bank in Europe; Feb. 18, 2015; XP055769888; Retrieved from the Internet: URL: https://www.ebi.ac.uk/pdbe/entry/pdb/4oej [retrieved on Jan. 28, 2021].
Gene Pe et al: "T2HUL2-1 [UniParc] Hide Protein Submitted name: Pe.pleurotolysin A Family & Domains Family and domain databases", , Nov. 13, 2013 (Nov. 13, 2013), XP055769881, Retrieved from the Internet: URL:https://www.uniprot.org/uniprot/T2HUL2 [retrieved on Jan. 28, 2021].
Gene Olya6: "Protein Ostreolysin A6 UniProtKB-P83467 (OLYA6_PLEOS)", , Oct. 16, 2013 (Oct. 16, 2013), XP055769879, Retrieved from the Internet: URL:https://www.uniprot.org/uniprot/P83467 [retrieved on Jan. 28, 2021].
Unknown: "Protein Submitted name: Erylysin A Family & Domains Family and domain databases InterPro View protein in InterPro IPR009413 , Aegerolysin-typ Pfam View protein in Pfam", , Dec. 15, 2009 (Dec. 15, 2009), XP055769882, Retrieved from the Internet: URL:https://www.uniprot.org/uniprot/DOFZZ2 [retrieved on Jan. 28, 2021].
Unknown: "Family & Domains UniProtKB—DOFZZ3", Dec. 15, 2009 (Dec. 15, 2009), XP055769904, Retrieved from the Internet: URL:https://www.uniprot.org/uniprot/DOFZZ3 [retrieved on Jan. 28, 2021].
RecName: Full=Ostreolysin A6; GenBank Accession No. P83467.2; Oct. 16, 2013 (Oct. 16, 2013); retrieved from the Internet: URL: https://www.ncbi.nlm.nih.gov/protein/550544293?sat=17&satkey=39241965.
Pe.pleurotolysin A [Pleurotus eryngii]; GenBank Accession No. BAN83906.1; Jan. 16, 2014 (Jan. 16, 2016); retrieved from the Internet: URL: https://www.ncbi.nlm.nih.gov/protein/BAN83906.1.
Erylysin A [Pleurotus eryngii]; GenBank Accession No. BAI45247.1; Oct. 22, 2009 (Oct. 22, 2009); retrieved from the Internet: URL: https://www.ncbi.nlm.nih.gov/protein/BAI45247.1.
Chain A, Pleurotolysin B; GenBank Accession No. 4OEJ_A; Feb. 18, 2015 (Feb. 18, 2015); retrieved from the Internet: URL: https://www.ncbi.nlm.nih.gov/protein/757819080?sat=48&satkey=132695392.
Erylysin A [Pleurotus eryngii]; GenBank Accession No. BAI45248.1; Oct. 22, 2009 (Oct. 22, 2009); retrieved from the Internet : URL: https://www.ncbi.nlm.nih.gov/protein/BAI45248.1.
Centre for Advanced Molecular Imaging; Carnivorous mushrooms reveal human immune trick; Retrieved from the Internet: URL: https://imagingcoe.org/carnivorous-mushrooms-reveal-human-immune-trick/; Feb. 5, 2015 (Feb. 5, 2015) [retrieved on Feb. 10, 2023].
Office Action dated Feb. 14, 2023, for corresponding Canadian Patent Application No. 3,077,263.

(56) References Cited

OTHER PUBLICATIONS

Jaka Razinger et al.; Applications of aegerolysinlike proteins for detection and eradication of pests; ResearchGate GmbH; downloaded Nov. 27, 2017.
Cyril F. Reboul et al.; Giant MACPF/CDC pore forming toxins: A class of their own; Biochimica et Biophysica Acta 1858; 2016; pp. 475-485.
Matej Butala et al.; Aegerolysins: Lipid-binding proteins with versatile functions; Seminars in Cell & Developmental Biology 72; 2017; pp. 142-151.
Ostreolysin A6; Origin amino acid sequence; National Library of Medicine; https://www.ncbi.nlm.nih.gov/protein/550544293?sat=46&satkey=116208113; published May 10, 2017; retrieved Aug. 12, 2022.
Pe. pleurotolysin A; Origin amino acid sequence; National Library of Medicine; https://www.ncbi.nlm.nih.gov/protein/BAN83906.1; published Jan. 16, 2014; retrieved Aug. 12, 2022.
Erylysin A; Origin amino acid sequence; National Library of Medicine; https://www.ncbi.nlm.nih.gov/protein/BAI45247.1; published Oct. 22, 2009; retrieved Aug. 12, 2022.
Pleurotolysin B; Origin amino acid sequence; National Library of Medicine; https://www.ncbi.nlm.nih.gov/protein/757819080?sat=48&satkey=132695392; published Feb. 18, 2015; retrieved Aug. 12, 2022.
Erylysin B; Origin amino acid sequence; National Library of Medicine; https://www.ncbi.nlm.nih.gov/protein/BAI45248.1?report=genbank&log$-protalign&blast_rank=1&RID=FC72UNF8016; published Oct. 22, 2009; retrieved Aug. 12, 2022.
Notification of First Office Action dated Aug. 23, 2022 for corresponding Chinese Patent Application No. 2017800954149, and English translation.

* cited by examiner

OlyA6 (SEQ ID NO: 1)

MAYAQWVIIIIHNVGSQDVKIKNLKASWGKLHADGDKDAEVSASNYEGKIVKPDEKLQINACGRSDAAEGTTGT
FDLVDPADGDKQVRHFYWDCPWGSKTNTWTVSGSNTKWMIEYSGQNLDSGALGTITVDTLKKGN

PlyA2 (SEQ ID NO: 2)

MAYAQWVIIIHNVGSKDVKIVNLKPSWGKLHADGDKDTEVSASKYEGTVIKPDEKLQINACGRSDAAEGTTGTF
DLVDPADGDKQVRHFYWDCPWGSKANTWTVSGSNTKWMIEYSGQNLDSGALGTITVDTLKKGN

EryA (SEQ ID NO: 3)

MAYAQWVIILIHNVGQQNVKIKNLNASWGKLYADGDKDTEVPASKYEGMVIAPDDQVQINACGREDAAEGTT
GTFDLVDPNDSDKQVRHFAWDCPWGTKANSWVVGGSNSKWMIEYTGQNLDSGALGTITVNTLRIGN

PlyB (SEQ ID NO: 4)

MEAVLSRQAATAEAIGRFQDSSTSVGLVAGSPSTRIRRQADNVVLKSTSQAGDTLNDVIQDPTRRNKLINDNNLL
KGIIMGRDGPVPSSRELIVRPDTLRAIINNRATIETTTMEAEFTETLMESNYNSASVKVSAPFITANSEYSESSSFKN
TETEKSMYTSSRYLFPQGRIDFTTPDSGFDDVIKLSPQFTSGVQAALAKATGTEKREALQNLFQEYGHVFRTKVHI
GGVLSAHTMETFSRSENETEVKQDVKAGLEGAVKGWGGGATAGHGNTQGTITTSQNRKLNVKYIVNGGDYTKI
QNTEEWVASTNQSEHWRVIEVTEVTAVADLLPQPIRGQVKDLLKPLLGKWVDVEKVPGLESLPVSVYRPKGAIPA
GWFWLGDTADASKALLVKPTLPARSGRNPALTSLHQGSGMTEQPFVDLPQYQYLSTYFGSFAHDTPPGSTLRGL
RPDHVLPGRYEMHGDTISTAVYVTRPVDVPFPEDECFDLKSLVRVKLPGSGNPPKPRSALKKSMVLFDSGEK

EryB (SEQ ID NO: 5)

MAAVLSRQAATAEAVERFQDSSTSVGLVAGSPSRIRRQADNVVLKSISQAGDTLNDVIQDPTRRNKLINDNNLLK
GIIMGRDGPVPSSRELIERPDTLRAIINNRATIETTTVEAEFTETLMESNYNSASVKVSAPFVTANSEYSESSSFKNT
ETEKSMYTSSRYLFPQGRIDFTMPDSGFDDVIKLSPQFTSGVQAALAKATGTEKREALQDLFLEYGHVFRTKVHIG
GVLSAHTMETFSRSENETEVKQDIKAGLEGAVKGWGGGATAGHGNTQGTITTSQNRKLDVKYIVNGGDYTKIQ
NTEEWVASTNQSEHWRVIEVTEVTAVADLLPQPIRGQVKDLLKPLLGKWVDVEKVPGLESFPVSVYRPKDAIPAG
WFWLGDTADASKALLVKPTLPARSGRNPALTSLHESSGMTEQPFVDLPQYQYLSTYFGSFAYDTPPGSTLRGLRP
DHILPGRYEMHGDTIGTAVYVTRPVDVPFPEDECFDLKSVVRVKLPGSGNPPKPRWALKKSMVLFDSGEE

A
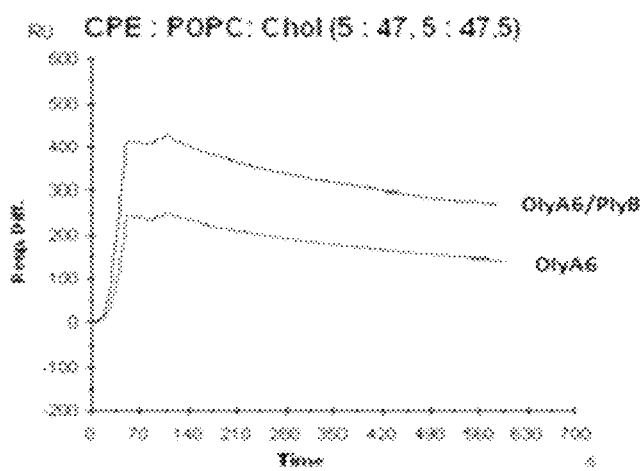
B
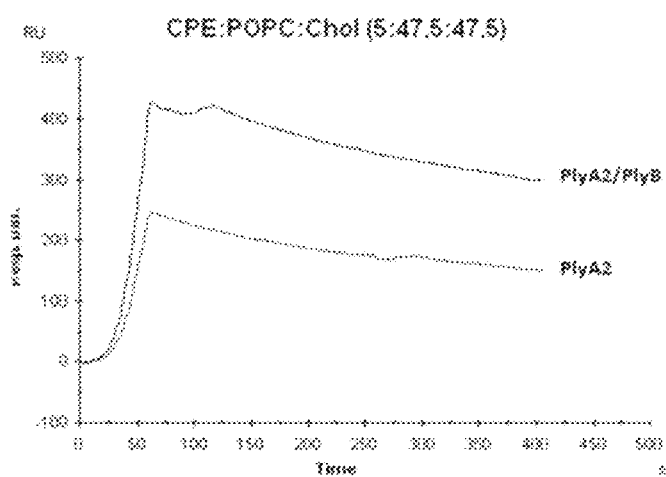
C
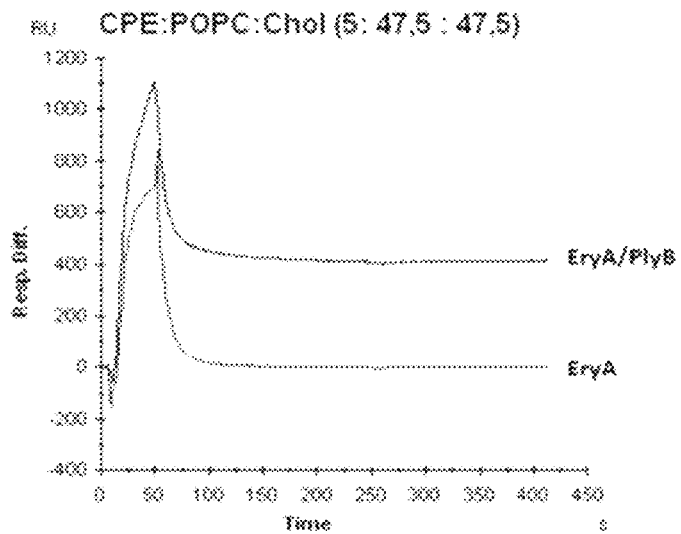
Figure 8

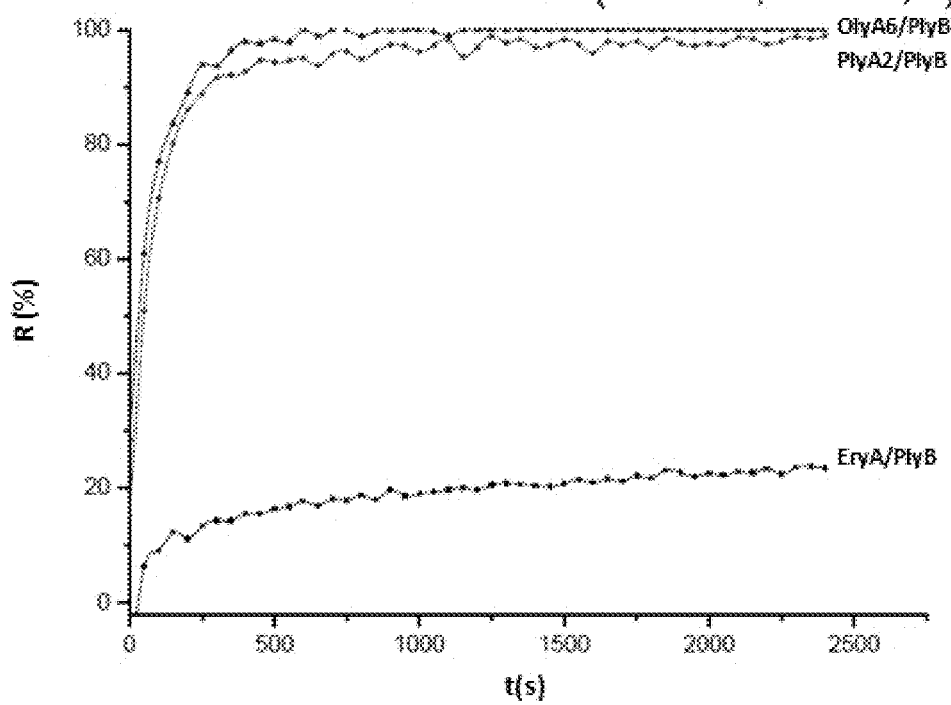
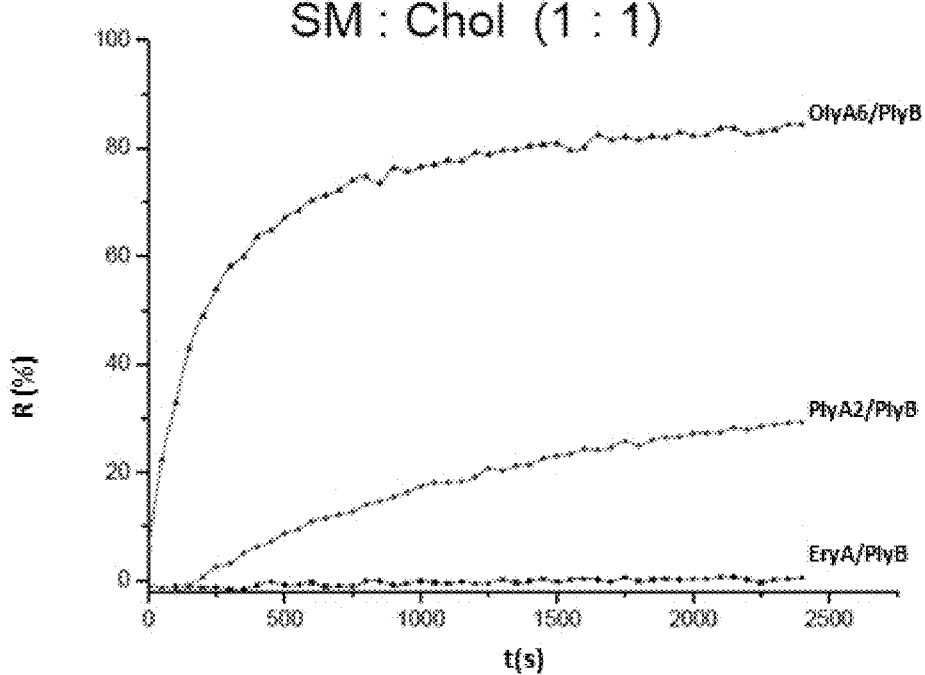
Figure 9

BIO-PESTICIDES FOR CONTROLLING PLANT PESTS

This application is a national phase of International Application No. PCT/EP2017/074877 filed Sep. 29, 2017 and published in the English language, which is incorporated herein by reference.

TECHNICAL FIELD OF THE INVENTION

The present invention falls within the scope of plant protection and relates to cytolytic bi-component protein complexes consisting of a plurality of molecules, such as at least 20 molecules of a member of the aegerolysin family and a plurality of molecules, such as at least 10 molecules of a member of the MACPF superfamily, and particularly to their use for controlling a plant pest, such as for controlling Colorado potato beetle (*Leptinotarsa decemlineata*) or Western corn rootworm (*Diabrotica virgifera virgifera*). More specifically, the invention relates to cytolytic bi-component protein complexes formed by a plurality of molecules of one of the aegerolysins ostreolysin A6 (OlyA6), pleurotolysin A2 (PlyA2) and erylysin A (EryA) with a plurality of molecules of pleurotolysin B (PlyB) or similar proteins, which have been shown to be toxic for the aforementioned agricultural pest insects.

TECHNICAL PROBLEM

Synthetic chemical pesticides have been the primary tools used to control Colorado potato beetle (CPB) and Western corn rootworm (WCR). Biological pesticides, such as the insecticidal proteins derived from *Bacillus thuringiensis* have played an important role as alternative for chemical pesticides. However, due to the constant evolution of resistance to pesticides, there is a continuous need for new bio-pesticides that will target specific molecular targets in pests.

STATE OF THE ART

CPB and WCR have the biggest economic impact and cause enormous damage to potatoes and maize crops (Alyokhin et al., 2008; Gassmann et al., 2011; Jakka et al., 2016). Current methods for controlling CPB and WCR include chemical pesticides that are facing serious problems, due to constant evolution of pesticide resistance (Meinke et al., 1998; Alyokhin et al., 2008; Pereira et al., 2015; Alyokhin et al., 2015; Jakka et al., 2016). Additional problems are the residues of chemical pesticides in food or feed, environmental concerns (Devine et al., 2007), and human health issues. The search for alternative biopesticides is therefore of the utmost importance.

CPB has been driving the development of the modern insecticidal industry since its early beginnings (Casagrande, 1987). Chemical pesticides, as well as some endotoxins from *Bacillus thuringiensis* subsp. *tenebrionis*, are generally in use for CPB control. Despite constant development of new pesticides, the problem due to the developing resistance through different mechanisms remains (Alyokhin et al., 2008).

For WCR control, European and American farmers apply granular insecticides or use insecticide-treated seeds. Foliar insecticides are also occasionally applied against adults (Meissle et al., 2009). However, these practices can cause serious health and environmental problems. Alternatively, WCR is controlled by genetically modified maize that expresses Cry toxins from *Bacillus thuringiensis* (Bt-maize), or by agronomic practices, such as crop rotation (Meissle et al., 2009). However, WCR has evolved resistance to Bt-maize, and has adapted to crop rotation (Gassman et al., 2012; Chu et al., 2014; Jakka et al., 2016). Biological control options have been recommended for WCR in south-eastern Europe in 1998 (Kuhlmann and Burgt, 1998).

Aegerolysins are low molecular (~15-20 kDa), acidic, beta-structured proteins, found in several eukaryotic and bacterial taxa (Berne et al., 2009; Novak et al., 2015; Butala et al., 2017). The common feature of aegerolysins is their interaction with specific lipids in biological membranes (Sepčić et al., 2004; Ota et al., 2013; Skočaj et al., 2014; Bhat et al., 2015). Aegerolysins from the fungal genus *Pleurotus* specifically target ceramide phosphoethanolamines (CPE) (FIG. 1), which are the major membrane sphingolipids of invertebrates (particularly insects and molluscs), but are present only in trace amounts in higher taxa (Crone and Bridges, 1963; Itasaka et al., 1973; Vacaru et al., 2013; Bhat et al., 2015). Moreover, these aegerolysins can function as bi-component lytic complexes in combination with a 59-kDa MACPF (membrane-attack-complex/perforin)-protein targeting cell membranes (Tomita et al., 2004; Shibata et al., 2010; Ota et al., 2013; Lukoyanova et al., 2015). Similar binary and quaternary cytolytic complexes in which aegerolysins are combined with larger, non-aegerolysin protein partner(s) have been found also in bacteria *Clostridium bifermentas* subsp. *malaysia* (Quareshi et al., 2014), *Bacillus thuringiensis* (Masson et al., 2004, Kelker et al., 2014) and *Alcaligenes faecalis* (Yalpani et al., 2017). These heteromeric bacterial aegerolysin-based cytolytic complexes are being exploited as potent insecticides for specific pests. Cry34Ab1, an aegerolysin protein that belongs to the larger group of insect-specific Cry toxins, and its protein partner Cry35Ab1 are already in use (Bt-maize) as tools for controlling WCR larvae. Cry34Ab1 and its partner specifically bind to (glyco)protein receptors in the membrane of epithelial cells in insects midgut, where the damage occurs (Masson et al., 2004; Kaiser-Alexant et al., 2009; Gassman et al., 2011). However, WCR larvae have recently developed resistance for Bt-maize that produces Cry34Ab1/Cry35Ab1 (Ludwick et al., 2017).

Aegerolysins from fungal genus *Pleurotus* (OlyA6, PlyA2, EryA) (SEQ ID NOs: 1-3 in FIG. 2) in combination with their specific protein partner, PlyB (SEQ ID NO: 4 in FIG. 2), represent novel promising biopesticides for controlling CPB and WCR. The ability of aegerolysins from the fungal genus *Pleurotus* to target CPE, and to form transmembrane pores in combination with PlyB, means that they can be used as pest-control agents. Moreover, the chances of evolving resistance to them should be minute, due to the fact that they interact with the membrane lipid receptor, and not with pest proteins that are prone to variation and thus evolvement of resistance to a pesticide.

SUMMARY OF THE INVENTION

The present invention can be summarized by the following items:
1. Use of a bi-component protein complex consisting of a plurality of molecules, such as at least 20 molecules of a member of the aegerolysin family and a plurality of molecules, such as at least 10 molecules of a member of the MACPF superfamily for controlling a plant pest.
2. The use according to item 1, where the bi-component protein complex consists of 20 to 30 molecules of a member of the aegerolysin family and 10 to 15 molecules of a member of the MACPF superfamily.
3. The use according to item 1 or 2, wherein the ratio of molecules of a member of the aegerolysin family to molecules of a member of the MACPF superfamily is 2:1.
4. The use according to any one of items 1 to 3, wherein the bi-component protein complex consists of 20 molecules of a member of the aegerolysin family and 10 molecules of a member of the MACPF superfamily, or consists of 22 molecules of a member of the aegerolysin family and 11 molecules of a member of the MACPF superfamily, or consists of 24 molecules of a member of the aegerolysin family and 12 molecules of a member of the MACPF superfamily, or consists of 26 molecules of a member of the aegerolysin family and 13 molecules of a member of the MACPF superfamily, or consists of 28 molecules of a member of the aegerolysin family and 14 molecules of a member of the MACPF superfamily, or consists of 30 molecules of a member of the aegerolysin family and 15 molecules of a member of the MACPF superfamily.
5. The use according to any one of items 1 to 4, wherein the member of the aegerolysin family is an aegerolysin derived from a fungus of the genus *Pleurotus*.
6. The use according to any one of items 1 to 5, wherein the member of the aegerolysin family is selected from the group consisting of ostreolysin, pleurotolysin A and erylysin A.
7. The use according to any one of items 1 to 6, wherein the member of the aegerolysin family is ostreolysin, such as ostreolysin A6.
8. The use according to item 7, wherein the ostreolysin is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 1.
9. The use according to any one of items 1 to 6, wherein the member of the aegerolysin family is pleurotolysin A, such as pleurotolysin A2.
10. The use according to item 9, wherein the pleurotolysin A is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 2.
11. The use according to any one of items 1 to 6, wherein the member of the aegerolysin family is erylysin A.
12. The use according to item 11, wherein the erylysin A is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 3.
13. The use according to any one of items 1 to 12, wherein the member of the MACPF superfamily is a MACPF domain containing protein derived from a fungus of the genus *Pleurotus*.
14. The use according to any one of items 1 to 13, wherein the member of the MACPF superfamily is pleurotolysin B (PlyB) or erylysin B (Ery B).
15. The use according to any one of items 1 to 13, wherein the member of the MACPF superfamily is pleurotolysin B (PlyB).
16. The use according to item 15, wherein pleurotolysin B is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 4.
17. The use according to any one of items 1 to 13, wherein the member of the MACPF superfamily is erylysin B (Ery B).
18. The use according to item 17, wherein erylysin B (Ery B) is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 5.
19. The use according to any one of items 1 to 18, wherein the plant pest is an insect.
20. The use according to any one of items 1 to 19, wherein the plant pest is a herbivorous insect.
21. The use according to item 19 or 20, wherein the plant pest is a larva of the insect.
22. The use according to item 19 or 20, wherein the plant pest is an imago of the insect.
23. The use according to any one of items 19 to 22, wherein the insect is of the order Coleoptera.
24. The use according to any one of items 19 to 23, wherein the insect is of the family Chrysomelidae.
25. The use according to any one of items 19 to 24, wherein the insect is of the genus *Leptinotarsa*.
26. The use according to any one of items 19 to 24, wherein the insect is *Leptinotarsa decemlineata* (Colorado potato beetle).
27. The use according to any one of items 19 to 24, wherein the insect is of the genus *Diabrotica*.
28. The use according to any one of items 19 to 24, wherein the insect is *Diabrotica virgifera virgifera* (Western corn rootworm).
29. The use according to any one of items 19 to 24, wherein the insect is selected from the group consisting *Leptinotarsa decemlineata* (Colorado potato beetle) and *Diabrotica virgifera virgifera* (Western corn rootworm).
30. The use according to any one of items 1 to 24, wherein the plant pest is selected from Colorado potato beetle and Western corn rootworm.
31. The use according to any one of items 1 to 24, wherein the plant pest is Colorado potato beetle, such as Colorado potato beetle larvae.
32. The use according to any one of items 1 to 24, wherein the plant pest is Western corn rootworm.
33. A method for protecting a plant against a plant pest, comprising the step of: applying a composition comprising a plurality of molecules of a member of the aegerolysin family, a plurality of molecules of a member of the MACPF superfamily and a suitable carrier, such as a buffer solution, to a plant in need thereof.
34. A method for controlling a plant pest, comprising the step of: applying a composition comprising a plurality of molecules of a member of the aegerolysin family, a plurality of molecules of a member of the MACPF superfamily and a suitable carrier, such as a buffer solution, to a plant in need thereof.
35. The method according to item 33 or 34, wherein the member of the aegerolysin family is an aegerolysin derived from a fungus of the genus *Pleurotus*.
36. The method according to any one of items 33 to 35, wherein the member of the aegerolysin family is selected from the group consisting of ostreolysin, pleurotolysin A and erylysin A.

37. The method according to any one of items 33 to 36, wherein the member of the aegerolysin family is ostreolysin, such as ostreolysin A6.
38. The method according to item 37, wherein the ostreolysin is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 1.
39. The method according to any one of items 33 to 36, wherein the member of the aegerolysin family is pleurotolysin A, such as pleurotolysin A2.
40. The method according to item 39, wherein the pleurotolysin A is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 2.
41. The method according to any one of items 33 to 36, wherein the member of the aegerolysin family is erylysin A.
42. The method according to item 41, wherein the erylysin A is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 3.
43. The method according to any one of items 33 to 42, wherein the member of the MACPF superfamily is a MACPF domain containing protein derived from a fungus of the genus *Pleurotus*.
44. The method according to any one of items 33 to 43, wherein the member of the MACPF superfamily is pleurotolysin B (PlyB) or erylysin B (Ery B).
45. The method according to any one of items 33 to 43, wherein the member of the MACPF superfamily is pleurotolysin B (PlyB).
46. The method according to item 45, wherein pleurotolysin B is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 4.
47. The method according to any one of items 33 to 43, wherein the member of the MACPF superfamily is erylysin B (Ery B).
48. The use according to item 47, wherein erylysin B (Ery B) is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 5.
49. The method according to any one of items 33 to 48, wherein the molar ratio between the member of the aegerolysin family and the member of the MACPF superfamily is in the range from about 3:1 to about 1000:1, such as about 5:1, about 10:1, about 20:1, about 25:1, about 30:1, about 40:1, about 50:1, about 60:1, about 70:1, about 80:1, about 90:1, about 100:1, about 200:1, about 300:1, about 400:1, about 500:1, about 600:1, about 700:1, about 800:1, or about 900:1, or about 1000:1.
50. The method according to any one of items 33 to 49, wherein the plant pest is an insect.
51. The method according to any one of items 33 to 50, wherein the plant pest is a herbivorous insect.
52. The method according to item 50 or 51, wherein the plant pest is a larva of the insect.
53. The method according to item 50 or 51, wherein the plant pest is an imago of the insect.
54. The method according to any one of items 50 to 53, wherein the insect is of the order Coleoptera.
55. The method according to any one of items 50 to 54, wherein the insect is of the family Chrysomelidae.
56. The method according to any one of items 50 to 55, wherein the insect is of the genus *Leptinotarsa*.
57. The method according to any one of items 50 to 55, wherein the insect is *Leptinotarsa decemlineata* (Colorado potato beetle).
58. The method according to any one of items 50 to 55, wherein the insect is of the genus *Diabrotica*.
59. The method according to any one of items 50 to 55, wherein the insect is *Diabrotica virgifera virgifera* (Western corn rootworm).
60. The method according to any one of items 50 to 55, wherein the insect is selected from the group consisting *Leptinotarsa decemlineata* (Colorado potato beetle) and *Diabrotica virgifera virgifera* (Western corn rootworm).
61. The method according to any one of items 33 to 49, wherein the plant pest is selected from Colorado potato beetle and Western corn rootworm.
62. The method according to any one of items 33 to 49, wherein the plant pest is Colorado potato beetle, such as Colorado potato beetle.
63. The method according to any one of items 33 to 49, wherein the plant pest is Western corn rootworm.
64. Use of a bi-component protein complex as defined in any one of items 1 to 18 or a composition as defined in any one of items 33 to 49 for the preparation of a plant protection agent.
65. A transgenic plant or progeny thereof which expresses or is capable of expressing a bi-component protein complex as defined in any one of items 1 to 18.
66. The transgenic plant or progeny thereof according to item 65, comprising (such as stably transformed with) one or more recombinant nucleic acid molecules comprising nucleotide sequences that encode a bi-component protein complex as defined in any one of items 1 to 18, said nucleotide sequences being operably linked to at least one promoter that is functional in said plant cell to cause the production of mRNA molecules.
67. The transgenic plant or progeny thereof according to item 65 or 66, wherein said transgenic plant or progeny thereof is a crop plant.
68. The transgenic plant or progeny thereof according to any one of items 65 to 67, wherein said transgenic plant or progeny thereof is a potato plant or maize plant.
69. The transgenic plant or progeny thereof according to any one of items 65 to 68, wherein said transgenic plant or progeny thereof is a potato plant.
70. The transgenic plant or progeny thereof according to any one of items 65 to 68, wherein said transgenic plant or progeny thereof is a maize plant.

BRIEF DESCRIPTION OF DRAWINGS

FIG. 2. Amino acid sequences of OlyA6 (SEQ ID NO: 1), PlyA2 (SEQ ID NO: 2), EryA (SEQ ID NO: 3), PlyB (SEQ ID NO: 4) and EryB (SEQ ID NO: 5).

Figure 6:
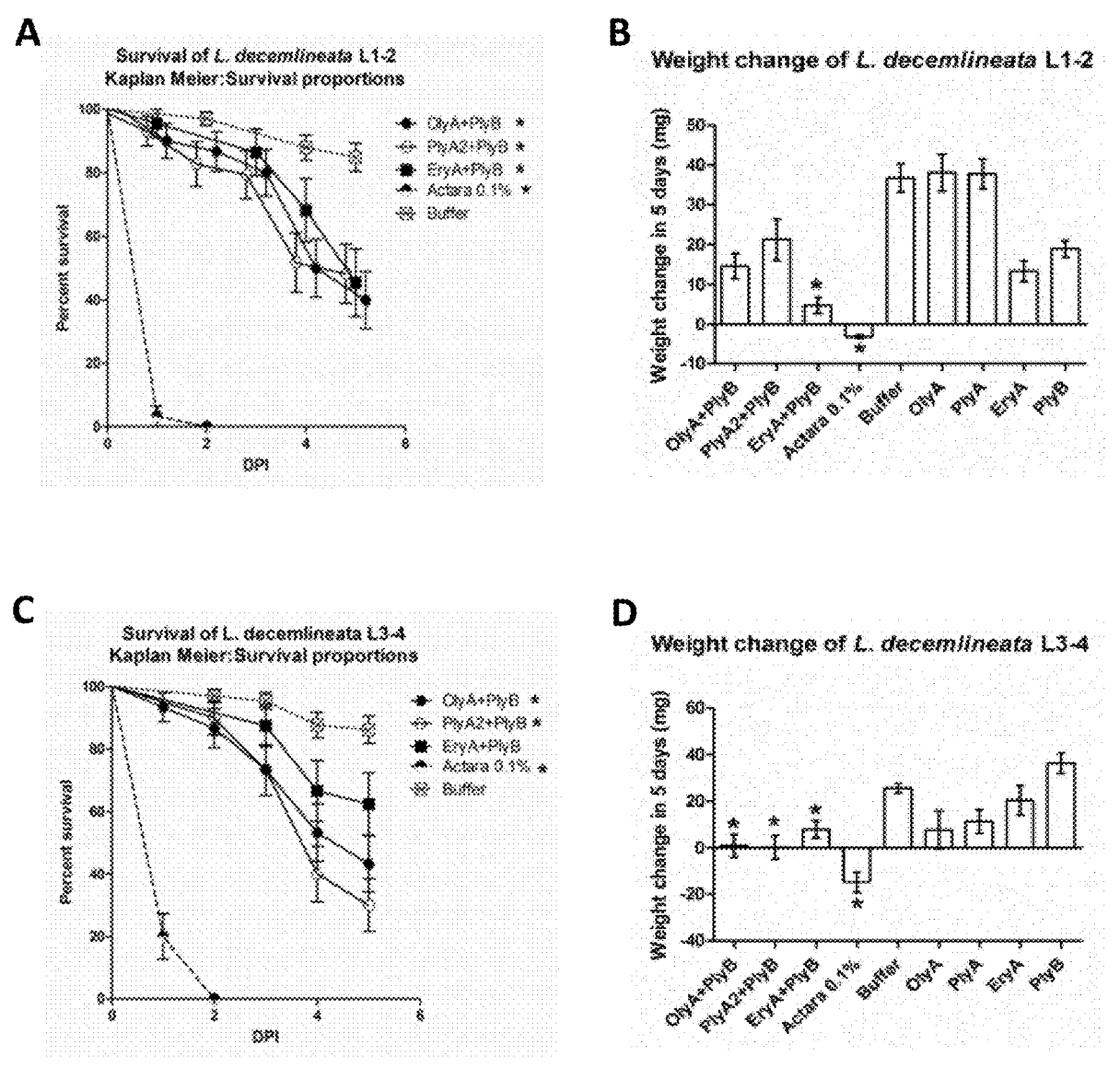

FIG. 6. Survival rate and weight change of Colorado potato beetle (CPB) during the feeding bioassay. Feeding of CPB larvae with leaf disks treated with OlyA6/PlyB, PlyA2/PlyB or EryA/PlyB protein mixtures (0.5 mg/mL for OlyA6, PlyA2, EryA and 0.04 mg/mL for PlyB) caused significant larval mortality on day 5 after initiation of feeding in the young larval group (L1+L2) (A). Only EryA/PlyB caused significant weight change in the young larval group (B). EryA/PlyB did not cause significant larval mortality in the old larval group (L3+L4) (C), while showing significant weight change (D). OlyA6/PlyB and PlyA2/PlyB caused significant larval mortality (C) in the old group as well as significant weight change (D). In L1 and L2, the pronotum is entirely black. In L3, the anterior margin of the pronotum appears orange-brown. In L4, about half the pronotum is light brown anteriorly. Asterisks indicate significant differences between the tested protein mixtures and buffer, which was used as a negative control ($P<0.05$).

FIG. 7. Feeding bioassay on Western corn rootworm (WCR). Protein mixtures (OlyA6/PlyB, PlyA2/PlyB or EryA/PlyB) and artificial diet were mixed (1:1, v:v) and applied to each well. The final concentration of OlyA6, EryA or PlyA2 was 0.5 mg/mL and 0.04 mg/mL of PlyB. A single Western corn rootworm beetle was transferred to each well and observed for 7 days. OlyA6/PlyB caused significant mortality of adult WCR, resulting in a median survival time of 5 days. Asterisks indicate significant differences between the tested protein mixtures and buffer, which was used as a negative control ($P<0.05$).

FIG. 8. The interaction of OlyA6, PlyA2 or EryA, alone or in combination with PlyB, with lipid vesicles composed of CPE:POPC:Chol (5:47.5:47.5, mol:mol:mol). OlyA6 and PlyA2 were injected in concentration of 0.25 µM and EryA was injected in concentration of 5 µM. PlyB was injected in concentration 20 nM when combined with OlyA6 and PlyA2, and 0.4 µM when combined with EryA. OlyA6 (A), PlyA2 (B) and EryA (C) specifically interact with membranes containing CPE and their interaction is stabilized in the presence of PlyB. CPE, ceramide phosphoethanolamine; POPC, palmitoyl-2-oleoyl-sn-glycero-3-phosphocholine; Chol, cholesterol.

FIG. 9. Lytic activity of OlyA6/PlyB, PlyA2/PlyB and EryA/PlyB. Tested protein mixtures OlyA6/PlyB and PlyA2/PlyB (10 µg/mL for OlyA6, PlyA2 or EryA and 0.8 µg/mL for PlyB) show permeabilization of artificial lipid vesicles containing CPE (A) as well as vesicles composed of SM:Chol (1:1, mol:mol) (B), while EryA/PlyB (10 µg/mL for EryA and 0.8 µg/mL for PlyB) is lytic only for vesicles containing CPE. CPE, ceramide phosphoethanolamine; POPC, palmitoyl-2-oleoyl-sn-glycero-3-phosphocholine; Chol, cholesterol; SM, sphingomyelin.

DETAILED DESCRIPTION OF THE INVENTION

Figure 1:
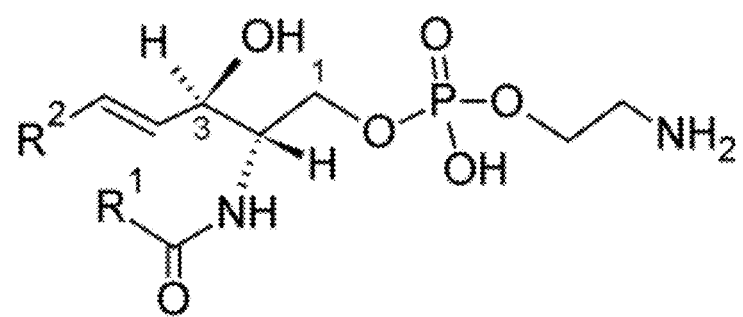
FIG. 1. Structure of ceramide phophoethanolamines (CPE). CPEs are composed of a ceramide residue (long-chain nitrogen base, which is amide-bonded to a 12-24 C atom fatty acid, designated as $R^2$) linked via 1-hydroxy group by a phosphodiester bonding to ethanolamine. The long-chain nitrogen base is either 1,3-dihydroxy C14:1, 1,3-dihydroxy C16:1 or 1,3-dihydroxy C18:1, indicated by $R^1$.
Figure 3:
FIG. 3. Feeding bioassay on Colorado potato beetle (CPB). Each potato leaf disk was soaked in OlyA6/PlyB, PlyA2/PlyB or EryA/PlyB mixture (0.5 mg/mL for OlyA6, PlyA2 or EryA and 0.04 mg/mL for PlyB) for 5 min and then transferred in each well on the microplate, to which a Colorado potato beetle larva was added. The survival rate was measured daily for 5 days. The weight of the larvae was measured on day 1 and day 5.
Figure 4:
FIG. 4. Feeding bioassay on Western corn rootworm. Protein mixtures (PlyA2/PlyB) and artificial diet were mixed (1:1, v:v) and applied in each well. The final protein concentration was 0.5 mg/mL of PlyA2 and 0.04 mg/mL of PlyB. A single Western corn rootworm beetle was transferred in each well and observed for 7 days.
Figure 5:
FIG. 5. Comparison of the development between OlyA6/PlyB-treated Colorado potato beetle (CPB) larvae and buffer-treated larvae (day 5). Buffer-treated CPB young larvae showed constant increase in weight and development (A), while CPB larvae treated with OlyA6/PlyB showed no weight change between day 1 and day 5, probably as a result of changed feeding behaviour after day 1 (B).

The present invention relates to cytolytic bi-component protein complexes consisting of a plurality of molecules, such as at least 20 molecules of a member of the aegerolysin family and a plurality of molecules, such as at least 10 molecules of a member of the MACPF superfamily, and particularly to their use for controlling a plant pest, such as for controlling Colorado potato beetle (*Leptinotarsa decemlineata*) or Western corn rootworm (*Diabrotica virgifera virgifera*). The present invention thus provides cytolytic bi-component protein complexes consisting of a plurality of molecules of a member of the aegerolysin family and a plurality of molecules of a member of the MACPF superfamily which are useful as pesticides.

As described in the Examples, cytolytic bi-component protein complexes composed of molecules of a member of the aegerolysin family and molecules of a member of the MACPF superfamily show toxic effect when ingested by invertebrates, particularly insects. These results indicate that the bi-component protein complexes damage the gut membranes. The subject of the invention thus indicates that bi-component protein complexes consisting of a plurality of molecules of a member of the aegerolysin family, such as OlyA6, PlyA2 or EryA, and a plurality of molecules of a member of the MACPF superfamily, such as PlyB, can serve as alternative biopesticides that can reduce the risk to the environment and to human health.

According to one aspect, the present invention provides the use of a bi-component protein complex consisting of a plurality of molecules of a member of the aegerolysin family and a plurality of molecules of a member of the MACPF superfamily for controlling a plant pest.

With >>plurality of molecules<< it is meant any number of molecules of a member of the aegerolysin family and any number of molecules of a member of the MACPF superfamily which allows the formation of transmembrane pores.

The bi-component protein complex may, for example, consist of 20 to 30 molecules of a member of the aegerolysin family and 10 to 15 molecules of a member of the MACPF superfamily.

Thus, according to certain embodiments, the bi-component protein complex consists of 20 to 30 molecules of a member of the aegerolysin family and 10 to 15 molecules of a member of the MACPF superfamily. According to certain embodiments, the bi-component protein complex consists of 22 to 30 molecules of a member of the aegerolysin family and 11 to 15 molecules of a member of the MACPF superfamily. According to certain embodiments, the bi-component protein complex consists of 24 to 30 molecules of a member of the aegerolysin family and 12 to 15 molecules of a member of the MACPF superfamily. According to certain embodiments, the bi-component protein complex consists of 26 to 30 molecules of a member of the aegerolysin family and 13 to 15 molecules of a member of the MACPF superfamily. According to certain embodiments, the bi-component protein complex consists of 28 to 30 molecules of a member of the aegerolysin family and 14 to 15 molecules of a member of the MACPF superfamily. According to certain embodiments, the bi-component protein complex consists of 22 to 28 molecules of a member of the aegerolysin family and 11 to 14 molecules of a member of the MACPF superfamily.

Generally, the bi-component protein complex is formed by a plurality of molecules of a member of the aegerolysin family and a plurality of molecules of a member of the MACPF superfamily in a ratio 2:1. In other words, the ratio of molecules of a member of the aegerolysin family to molecules of a member of the MACPF superfamily is 2:1.

According to some embodiments, the bi-component protein complex consists of 20 molecules of a member of the aegerolysin family and 10 molecules of a member of the MACPF superfamily, or consists of 22 molecules of a member of the aegerolysin family and 11 molecules of a member of the MACPF superfamily, or consists of 24 molecules of a member of the aegerolysin family and 12 molecules of a member of the MACPF superfamily, or consists of 26 molecules of a member of the aegerolysin family and 13 molecules of a member of the MACPF superfamily, or consists of 28 molecules of a member of the aegerolysin family and 14 molecules of a member of the MACPF superfamily, or consists of 30 molecules of a member of the aegerolysin family and 15 molecules of a member of the MACPF superfamily.

According to particular embodiments, the bi-component protein complex consists of 26 molecules of a member of the aegerolysin family and 13 molecules of a member of the MACPF superfamily.

Since the bi-component protein complex can be (or is) formed in situ it will be understood that the molecular composition and frequency may vary, meaning that different bi-component protein complexes formed of the same components may be present on the plane of the lipid bilayer varying in their molecular composition and frequency. As a non-limiting example, Lukoyanova et al. (2015) and Ota et al. (2013), dealing with structures of PlyA/PlyB and OlyA6/PlyB based complexes, have shown that the pores formed by aegerolysins and PlyB in situ usually come in the following molecular compositions (the % denotes the frequency of different molecular composition on the plane of the lipid bilayer): 26 PlyA:13 PlyB (75%), 24 PlyA:12 PlyB (15%), 22 PlyA:11 PlyB (5%), and 28 PlyA:14 PlyB (5%). Hence, the bi-component protein complex may be a mixture of component protein complexes formed by the same components varying in their molecular composition.

Members of the aegerolysin family as well as members of the MACPF superfamily from a range of fungi and bacteria have been described in the scientific literature (e.g. Ota et al., 2014; Butala et al., 2017; Anderluh et al., 2014). The aegerolysin family is a family of proteins which are characterized in that they contain an aegerolysin domain. The MACPF superfamily is a family of proteins which are characterized in that they contain a MACPF (Membrane Attack Complex/Perforin) domain. Members of the aegerolysin family specifically target ceramide phosphoethanolamines, which are major membrane sphingolipids of invertebrates (particular insects and molluscs). Some members of the MACPF superfamily have cytolytic activity, and those are useful according to the present invention.

Members of the aegerolysin family as well as members of the MACPF superfamily for use according to the present invention may be of fungal or bacterial origin. Non-limiting examples of members of the aegerolysin family include aegerolysins derived from a fungus of the genus *Pleurotus*, such as from *Pleurotus ostreatus* or *Pleurotus eryngii*. Non-limiting examples of members of the MACPF superfamily include MACPF-containing proteins derived from a fungus of the genus *Pleurotus*, such as from *Pleurotus ostreatus* or *Pleurotus eryngii*.

Therefore, according to certain embodiments, the member of the aegerolysin family is an aegerolysin derived from a fungus of the genus *Pleurotus*.

According to some embodiments, the member of the aegerolysin family is an aegerolysin derived from the fungus *Pleurotus ostreatus*. According to some other embodiments, the member of the aegerolysin family is an aegerolysin derived from the fungus *Pleurotus eryngii*.

According to certain embodiments, the member of the MACPF superfamily is a MACPF-containing protein derived from a fungus of the genus *Pleurotus*.

According to some embodiments, the member of the MACPF superfamily is a MACPF-containing protein derived from the fungus *Pleurotus ostreatus*. According to some other embodiments, the member of the MACPF superfamily is a MACPF-containing protein derived from the fungus *Pleurotus eryngii*.

Non-limiting examples of aegerolysins include ostreolysin, pleurotolysin A and erylysin A.

According to certain embodiments, the member of the aegerolysin family is selected from the group consisting of ostreolysin, pleurotolysin A and erylysin A.

According to some embodiments, the member of the aegerolysin family is ostreolysin, such as ostreolysin A6. According to some specific embodiments, the ostreolysin is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 1. According to some specific embodiments, the ostreolysin is a polypeptide comprising an amino acid sequence having at least 55% sequence identity with SEQ ID NO: 1. According to some specific embodiments, the ostreolysin is a polypeptide comprising an amino acid sequence having at least 60% sequence identity with SEQ ID NO: 1. According to some specific embodiments, the ostreolysin is a polypeptide comprising an amino acid sequence having at least 65% sequence identity with SEQ ID NO: 1. According to some specific embodiments, the ostreolysin is a polypeptide comprising an amino acid sequence having at least 70% sequence identity with SEQ ID NO: 1. According to some specific embodiments, the ostreolysin is a polypeptide comprising an amino acid sequence having at least 75% sequence identity with SEQ ID NO: 1. According to some specific embodiments, the ostreolysin is a polypeptide comprising an amino acid sequence having at least 80% sequence identity with SEQ ID NO: 1. According to some specific embodiments, the ostreolysin is a polypeptide comprising an amino acid sequence having at least 85% sequence identity with SEQ ID NO: 1. According to some specific embodiments, the ostreolysin is a polypeptide comprising an amino acid sequence having at least 90% sequence identity with SEQ ID NO: 1. According to some specific embodiments, the ostreolysin is a polypeptide comprising an amino acid sequence having at least 95% sequence identity with SEQ ID NO: 1. According to some specific embodiments, the ostreolysin is a polypeptide comprising an amino acid sequence having at least 97% sequence identity with SEQ ID NO: 1. According to some specific embodiments, the ostreolysin is a polypeptide comprising an amino acid sequence having at least 99% sequence identity with SEQ ID NO: 1. Such polypeptide(s) suitably has the same or similar property than the reference polypeptide of SEQ ID NO: 1, i.e. binding to CPEs and forming a cytolytic complex with pleurotolysin B and similar proteins. The property can be determined in accordance with the following membrane permeabilization test:

Membrane Permeabilization Test

1. Principle:

Calcein-loaded small unilamellar vesicles (SUVs) containing CPE are used in order to confirm the lytic activity of a polypeptide to be tested (i.e. a polypeptide having the indicated % sequence identity to an aegerolysin, such as ostreolysin of SEQ ID NO: 1—herein after >>test polypeptide<<) with the protein partner PlyB (SEQ ID NO: 4).

To prepare the SUVs, lipid films with defined molar proportions of lipids (CPE:POPC:Chol [5:47.5:47.5, mol:mol:mol]) are prepared by removing the organic solvent from lipid solutions by rotary evaporation and vacuum drying. Lipids, at final concentration of 5 mg/mL, are swollen in 80 mM calcein and vortexed vigorously to give multilamellar liposomes (MLVs). The suspension of MLVs is sonicated for 15 minutes on ice with 10 sec on/off cycles to prepare SUVs. Extra-vesicular calcein is removed from SUV suspension by gel filtration on a Sephadex G-50 (medium) column, where vesicle buffer composed of 140 mM NaCl, 20 mM TRIS.HCl, pH 8.0 is used as a mobile phase. The lytic activity of the protein complex is assayed using a fluorescence microplate reader at 25° C.

2. Procedure:

Protein mixtures comprising the test polypeptide and PlyB (12.5:1, mol:mol) are dispensed into a multi-well microplate at the following concentrations: 10 μg/mL test polypeptide combined with 0.8 μg/mL PlyB. The final volume of the proteins in each well of the microtiter plate, diluted in vesicle buffer (140 mM NaCl, 20 mM TRIS.HCl, pH 8.0), is 100 μl. Calcein-loaded SUVs (5 μg/mL) are added to the protein mixtures. The SUVs are excited at 485 nm and the intensity of the emitted fluorescence of released calcein is monitored at 535 nm for 30 min with 20 s intervals. The intensity of the emitted fluorescence at t=30 is determined as F. SUVs are fully lysed with 1 mM Triton X-100 (positive control), where $F_{max}$ is determined as a maximal fluorescence intensity following the lysis of all the SUVs. $F_0$ is the fluorescence of SUVs at t=30 in the absence of lytic protein mixtures, or in the absence of Triton X-100. The percentage of calcein release R (%) is calculated as:

$$R(\%) = \frac{F - Fo}{F\max - Fo} * 100$$

The protein complex can be considered as lytic when the R value is 5% of the positive control.

According to some embodiments, the member of the aegerolysin family is pleurotolysin A, such as pleurotolysin A2. According to some specific embodiments, the pleurotolysin A is a polypeptide comprising an amino acid sequence having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 2. According to some specific embodiments, the pleurotolysin A is a polypeptide comprising an amino acid sequence having at least 55% sequence identity with SEQ ID NO: 2. According to some specific embodiments, the pleurotolysin A is a polypeptide comprising an amino acid sequence having at least 60% sequence identity with SEQ ID NO: 2. According to some specific embodiments, the pleurotolysin A is a polypeptide comprising an amino acid sequence having at least 65% sequence identity with SEQ ID NO: 2. According to some specific embodiments, the pleurotolysin A is a polypeptide comprising an amino acid sequence having at least 70% sequence identity with SEQ ID NO: 2. According to some specific embodiments, the pleurotolysin A is a polypeptide comprising an amino acid sequence having at least 75% sequence identity with SEQ ID NO: 2. According to some specific embodiments, the pleurotolysin A is a polypeptide comprising an amino acid sequence having at least 80% sequence identity with SEQ ID NO: 2. According to some specific embodiments, the pleurotolysin A is a polypeptide comprising an amino acid sequence having at least 85 sequence identity with SEQ ID NO: 2. According to some specific embodiments, the pleurotolysin A is a polypeptide comprising an amino acid sequence having at least 90% sequence identity with SEQ ID NO: 2. According to some specific embodiments, the pleurotolysin A is a polypeptide comprising an amino acid sequence having at least 95% sequence identity with SEQ ID NO: 2. According to some specific embodiments, the pleurotolysin A is a polypeptide comprising an amino acid sequence having at least 97% sequence identity with SEQ ID NO: 2. According to some specific embodiments, the pleurotolysin A is a polypeptide comprising an amino acid sequence having at least 99% sequence identity with SEQ ID NO: 2. Such polypeptide(s) suitably has the same or similar property than the reference polypeptide of SEQ ID NO: 2, i.e. binding to CPEs and forming a cytolytic complex with pleurotolysin B and similar proteins. The property can be determined in accordance with the membrane permeabilization test described above.

According to some embodiments, the member of the aegerolysin family is erylysin A. According to some specific embodiments, the erylysin A is a polypeptide having at least 50%, such as at least 55%, at least 60%, at least 65%, at least 70%, at least 75%, at least 80%, at least 85%, at least 90%, at least 95%, at least 97% or at least 99% sequence identity with SEQ ID NO: 3. According to some specific embodiments, the erylysin A is a polypeptide having at least 55% sequence identity with SEQ ID NO: 3.

According to some specific embodiments, the erylysin A is a polypeptide having at least 60% sequence identity with SEQ ID NO: 3. According to some specific embodiments, the erylysin A is a polypeptide having at least 65% sequence identity with SEQ ID NO: 3. According to some specific embodiments, the erylysin A is a polypeptide having at least 70% sequence identity with SEQ ID NO: 3. According to some specific embodiments, the erylysin A is a polypeptide having at least 75% sequence identity with SEQ ID NO: 3. According to some specific embodiments, the erylysin A is a polypeptide having at least 80% sequence identity with SEQ ID NO: 3. According to some specific embodiments, the erylysin A is a polypeptide having at least 85% sequence identity with SEQ ID NO: 3. According to some specific embodiments, the erylysin A is a polypeptide having at least 90% sequence identity with SEQ ID NO: 3. According to some specific embodiments, the erylysin A is a polypeptide having at least 95% sequence identity with SEQ ID NO: 3. According to some specific embodiments, the erylysin A is a polypeptide comprising an amino acid sequence having at least 97% sequence identity with SEQ ID NO: 3. According to some specific embodiments, the erylysin A is a polypeptide comprising an amino acid sequence having at least 99% sequence identity with SEQ ID NO: 3. Such polypeptide(s) suitably has the same or similar property than the reference polypeptide of SEQ ID NO: 3, i.e. binding to CPEs and forming a cytolytic complex with pleurotolysin B and similar proteins. The property can be determined in accordance with the membrane permeabilization test described above.

Non-limiting examples of a member of the MACPF superfamily include pleurotolysin B (PlyB), erylysin B (Ery B) or a similar protein from the fungi *Sphaerobolus stellatus, Moniliophtora perniciosa, Trametes pubescens*, and *Heterobasidion irregulare*.

According to certain embodiments, the member of the MACPF superfamily is pleurotolysin B (PlyB) or erylysin B (Ery B).

According to some embodiments, the member of the MACPF superfamily is pleurotolysin B (PlyB). According to some specific embodiments, pleurotolysin B is a polypeptide comprising an amino acid sequence having at least 50%, such as at least 55%, at least 60%, at least 65%, at least 70%, at least 75% %, at least 80%, at least 85%, at least 90%, at least 95%, at least 97% or at least 99% sequence identity with SEQ ID NO: 4. According to some specific embodiments, pleurotolysin B is a polypeptide comprising an amino acid sequence having at least 55% sequence identity with SEQ ID NO: 4. According to some specific embodiments, pleurotolysin B is a polypeptide comprising an amino acid sequence having at least 60% sequence identity with SEQ ID NO: 4. According to some specific embodiments, pleurotolysin B is a polypeptide comprising an amino acid sequence having at least 65% sequence identity with SEQ ID NO: 4. According to some specific embodiments, pleurotolysin B is a polypeptide comprising an amino acid sequence having at least 70% sequence identity with SEQ ID NO: 4. According to some specific embodiments, pleurotolysin B is a polypeptide comprising an amino acid sequence having at least 75% % sequence identity with SEQ ID NO: 4. According to some specific embodiments, pleurotolysin B is a polypeptide comprising an amino acid sequence having at least 80% sequence identity with SEQ ID NO: 4. According to some specific embodiments, pleurotolysin B is a polypeptide comprising an amino acid sequence having at least 85% sequence identity with SEQ ID NO: 4. According to some specific embodiments, pleurotolysin B is a polypeptide comprising an amino acid sequence having at least 90% sequence identity with SEQ ID NO: 4. According to some specific embodiments, pleurotolysin B is a polypeptide comprising an amino acid sequence having at least 95% sequence identity with SEQ ID NO: 4. According to some specific embodiments, pleurotolysin B is a polypeptide comprising an amino acid sequence having at least at least 97% sequence identity with SEQ ID NO: 4. According to some specific embodiments, pleurotolysin B is a polypeptide comprising an amino acid sequence having at least 99% sequence identity with SEQ ID NO: 4. Such polypeptide(s) suitably has the same or similar cytolytic activity with ostreolysin, pleurotolysin A, erylysin A or a similar protein than the reference polypeptide of SEQ ID NO: 4. Particularly, such polypeptide(s) contains a functional MACPF domain. The cytolytic activity can be determined by suitable tests available to the skilled person, such as by hemolysis assay or by monitoring the calcein release from liposomes.

The cytolytic activity may, for example, be determined in accordance with the following membrane permeabilization test:

Membrane Permeabilization Test

1. Principle:

Calcein-loaded small unilamellar vesicles (SUVs) containing CPE are used in order to confirm the lytic activity of polypeptide to be tested (i.e. a polypeptide having the indicated % sequence identity to a member of the MACPF superfamily, such as pleurotolysin B of SEQ ID NO: 4 herein after >>test polypeptide<<) with one of the protein partners ostreolysin (SEQ ID NO: 1), pleurotolysin A (SEQ ID NO: 2) or erylysin A (SEQ ID NO: 3).

To prepare the SUVs, lipid films with defined molar proportions of lipids (CPE:POPC:Chol [5:47.5:47.5, mol:mol:mol]) are prepared by removing the organic solvent from lipid solutions by rotary evaporation and vacuum drying. Lipids, at final concentration of 5 mg/mL, are swollen in 80 mM calcein and vortexed vigorously to give multilamellar liposomes (MLVs). The suspension of MLVs is sonicated for 15 minutes on ice with 10 sec on/off cycles to prepare SUVs. Extra-vesicular calcein is removed from SUV suspension by gel filtration on a Sephadex G-50 (medium) column, where vesicle buffer composed of 140 mM NaCl, 20 mM TRIS.HCl, pH 8.0 is used as a mobile phase. The lytic activity of the protein complex is assayed using a fluorescence microplate reader at 25° C.

2. Procedure:

Protein mixtures comprising the test polypeptide and ostreolysin, pleurotolysin A or erylysin A (1:12.5, mol:mol) are dispensed into a multi-well microplate at the following concentrations: 10 μg/mL test aegerolysin combined with 0.8 μg/mL PlyB. The final volume of the proteins in each well of the microtiter plate, diluted in vesicle buffer (140 mM NaCl, 20 mM TRIS.HCl, pH 8.0), is 100 μL. Calcein-loaded SUVs (5 μg/mL) are added to the protein mixtures. The SUVs are excited at 485 nm and the intensity of the emitted fluorescence of released calcein is monitored at 535 nm for 30 min with 20 s intervals. The intensity of the emitted fluorescence at t=30 is determined F. SUVs are fully lysed with 1 mM Triton X-100 (positive control), where $F_{max}$ is determined as a maximal fluorescence intensity following the lysis of all the SUVs. $F_0$ is the fluorescence of SUVs at t=30 in the absence of lytic protein mixtures, or in the absence of Triton X-100. The percentage of calcein release R (%) is calculated as:

$$R(\%) = \frac{F - Fo}{F\max - Fo} * 100$$

The protein complex can be considered as lytic when the R value is ≥5% of the positive control.

According to some embodiments, the member of the MACPF superfamily is erylysin B (Ery B). According to some specific embodiments, erylysin B (Ery B) is a polypeptide comprising an amino acid sequence having at least 50%, such as at least 55%, at least 60%, at least 65%, at least 75% %, at least 80%, at least 85%, at least 90%, at least 95%, at least 97% or at least 99% sequence identity with SEQ ID NO: 5. According to some specific embodiments, erylysin B (Ery B) is a polypeptide comprising an amino acid sequence having at least 55% sequence identity with SEQ ID NO: 5. According to some specific embodiments, erylysin B (Ery B) is a polypeptide comprising an amino acid sequence having at least 60% sequence identity with SEQ ID NO: 5. According to some specific embodiments, erylysin B (Ery B) is a polypeptide comprising an amino acid sequence having at least 65% sequence identity with SEQ ID NO: 5. According to some specific embodiments, erylysin B (Ery B) is a polypeptide comprising an amino acid sequence having at least 70% sequence identity with SEQ ID NO: 5. According to some specific embodiments, erylysin B (Ery B) is a polypeptide comprising an amino acid sequence having at least 75% % sequence identity with SEQ ID NO: 5. According to some specific embodiments, erylysin B (Ery B) is a polypeptide comprising an amino acid sequence having at least 80% sequence identity with SEQ ID NO: 5. According to some specific embodiments, erylysin B (Ery B) is a polypeptide comprising an amino acid sequence having at least 85% sequence identity with SEQ ID NO: 5. According to some specific embodiments, erylysin B (Ery B) is a polypeptide comprising an amino acid sequence having at least 90% sequence identity with SEQ ID NO: 5. According to some specific embodiments, erylysin B (Ery B) is a polypeptide comprising an amino acid sequence having at least 95% sequence identity with SEQ ID NO: 5. According to some specific embodiments, erylysin B (Ery B) is a polypeptide comprising an amino acid sequence having at least 97% sequence identity with SEQ ID NO: 5. According to some specific embodiments, erylysin B (Ery B) is a polypeptide comprising an amino acid sequence having at least 99% sequence identity with SEQ ID NO: 5. Such polypeptide(s) suitably has the same or similar cytolytic activity with ostreolysin, pleurotolysin A, erylysin A or a similar protein than the reference polypeptide of SEQ ID NO: 5. Particularly, such polypeptide(s) contains a functional MACPF domain. The cytolytic activity can be determined by suitable tests available to the skilled person, such as by hemolysis assay or by monitoring the calcein release from liposomes. The cytolytic activity may, for example, be determined in accordance with the membrane permeabilization test described above.

According to certain embodiments, the member of the aegerolysin family is ostreolysin, such as ostreolysin A6, and the member of the MACPF superfamily is pleurotolysin B.

According to certain embodiments, the member of the aegerolysin family is pleurotolysin A, such as pleurotolysin A2, and the member of the MACPF superfamily is pleurotolysin B.

According to certain embodiments, the member of the aegerolysin family is erylysin A and the member of the MACPF superfamily is pleurotolysin B.

According to certain embodiments, the member of the aegerolysin family is ostreolysin, such as ostreolysin A6, and the member of the MACPF superfamily is erylysin B.

According to certain embodiments, the member of the aegerolysin family is pleurotolysin A, such as pleurotolysin A2, and the member of the MACPF superfamily is erylysin B.

According to certain embodiments, the member of the aegerolysin family is erylysin A and the member of the MACPF superfamily is erylysin B.

The bi-component protein complex may generally be used at a concentration ranging from about 1.5 µg/ml (0.1 µM of a member of the aegerolysin family in a 1000:1 molar ratio with a member of the MACPF superfamily) to 34.5 mg/ml (1 mM of a member of the aegerolysin family in a 3:1 molar ratio with a member of the MACPF superfamily). That is the concentration of the member of the aegerolysin family used is usually in the range of 0.1 µM to about 1 mM, such as from about 0.5 µM to about 1 mM, about 1 µM to about 1 mM, about 10 µM to about 1 mM, about 50 µM to about 1 mM, about 100 µM to about 1 mM, or about 500 µM to about 1 mM, about 0.1 µM to about 500 µM, 0.5 µM to about 500 µM, about 1 µM to about 500 µM, about 10 µM to about 500 µM, about 50 µM to about 500 µM, about 100 µM to about 500 µM, 0.5 µM to about 100 µM, about 1 µM to about 100 µM, about 10 µM to about 100 µM, or about 50 µM to about 100 µM. The member of the MACPF superfamily is used in appropriate amounts to obtain the desired molar ratio which is generally in the range from about 3:1 to about 1000:1.

The plant pest to be controlled by using a bi-component protein complex in accordance with the invention can be an insect, such as a herbivorous insect. Therefore, according to certain embodiments, the plant pest is an insect. According to some embodiments, the plant pest is a herbivorous insect.

The plant pest may be a larva and/or an imago of the insect. According to certain embodiments, the plant pest is a larva of the insect. According to certain embodiments, the plant pest is an imago of the insect.

The larva may be in any stage of larval development. According to certain embodiments, the larva is in a larval stage selected from the group consisting of L1, L2, L3, L4, and L5. According to certain embodiments, the larva is in a larval stage selected from L1, L2, L3, and L4. According to certain embodiments, the larva is in a larval stage selected from L1, L2, and L3. According to certain embodiments, the larva is in a larval stage selected from L1 and L2. According to certain embodiments, the larva is in a larval stage selected from the group consisting of L2, L3, L4, and L5. According to certain embodiments, the larva is in a larval stage selected from the group consisting of L2, L3 and L4. According to certain embodiments, the larva is in a larval stage selected from the group consisting of L2 and L3. According to certain embodiments, the larva is in a larval stage selected from the group consisting of L3 and L4. According to some embodiments, the larva is in larval stage L1. According to some embodiments, the larva is in larval stage L2. According to some embodiments, the larva is in larval stage L3. According to some embodiments, the larva is in larval stage L4. According to some embodiments, the larva is in larval stage L5.

According to certain embodiments, the insect is of the order Coleoptera.

According to some embodiments, the insect is of the family Chrysomelidae.

According to some particular embodiments, the insect is of the genus *Leptinotarsa*.

According to some specific embodiments, the insect is *Leptinotarsa decemlineata* (Colorado potato beetle).

According to some particular embodiments, the insect is of the genus *Diabrotica*.

According to some specific embodiments, the insect is *Diabrotica virgifera virgifera* (Western corn rootworm).

According to some particular embodiments, the insect is of the genus *Phyllotreta*.

According to some specific embodiments, the insect is *Phyllotreta* spp.

According to some specific embodiments, the insect is *Phyllotreta cruciferae*.

According to some specific embodiments, the insect is *Phyllotreta striolata*.

According to some specific embodiments, the insect is selected from the group consisting *Leptinotarsa decemlineata* (Colorado potato beetle) and *Diabrotica virgifera virgifera* (Western corn rootworm).

According to some particular embodiments, the insect is of the genus *Lilioceris*.

According to some specific embodiments, the insect is *Lilioceris merdigera*.

According to some specific embodiments, the insect is *Lilioceris lilii*.

According to some particular embodiments, the insect is of the genus *Crioceris*.

According to some specific embodiments, the insect is *Crioceris duodecimpunctata*.

According to some embodiments, the insect is of the family Scarabeidae.

According to some particular embodiments, the insect is of the genus *Melolontha*.

According to some specific embodiments, the insect is *Melolontha melolontha*.

According to some particular embodiments, the insect is of the genus *Popillia*.

According to some specific embodiments, the insect is *Popillia japonica* (Japanese beetle).

According to some embodiments, the insect is of the family Elateridae.

According to some particular embodiments, the insect is of the genus *Agriotes*.

According to some specific embodiments, the insect is *Agriotes* spp.

According to some specific embodiments, the insect is *Agriotes lineatus*.

According to some specific embodiments, the insect is *Agriotes obscurus*.

According to some specific embodiments, the insect is *Agriotes ustulatus*.

According to some specific embodiments, the insect is *Agriotes sputator*.

According to some embodiments, the insect is of the family Byturidae.

According to some particular embodiments, the insect is of the genus *Byturus*.

According to some specific embodiments, the insect is *Byturus tomentosus*.

According to certain embodiments, the plant pest is a coleopteran insect pest.

According to particular embodiments, the plant pest is selected from Colorado potato beetle, Western corn rootworm and other coleopteran insect pests.

According to some embodiments, the plant pest is a Colorado potato beetle.

According to some embodiments, the plant pest is Western corn rootworm.

According to some embodiments, the plant pest is cabbage flea beetle.

According to some embodiments, the plant pest is Japanese beetle.

According to some embodiments, the plant pest is May beetle.

According to some embodiments, the plant pest is Wireworm.

According to some embodiments, the plant pest is Raspberry beetle.

The present invention further provides a method for protecting a plant against a plant pest, comprising the step of: applying a composition comprising a plurality of molecules of a member of the aegerolysin family, a plurality of molecules of a member of the MACPF superfamily and a suitable carrier, such as a buffer solution, to a plant in need thereof.

The present invention further provides a method for controlling a plant pest, comprising the step of: applying a composition comprising a plurality of molecules of a member of the aegerolysin family, a plurality of molecules of a member of the MACPF superfamily and a suitable carrier, such as a buffer solution, to a plant in need thereof.

Generally, the member of the aegerolysin family and the member of the MACPF superfamily are present in the composition in a free, non-complexed form. Once the composition is applied to a plant of interest and molecules of the member of the aegerolysin family and molecules of the member of the MACPF superfamily are ingested by the insect, bi-component protein complexes as described herein are formed in situ on the plasmalemma of epithelial cells of the midgut, leading to the perforation of the gut, and subsequently to the death of the insect.

It is understood that all details provided herein with respect to the bi-component protein complexes, particularly with respect to the member of the aegerolysin family and the member of the MACPF superfamily, and the plant pest, including all embodiments, apply mutatis mutandis to the methods of the present invention.

Generally, the composition can be applied to a plant in need thereof in any suitable dose, frequency and method of administration.

The composition may suitably be in liquid form, and may be applied by spraying, drenching or dropping onto the plant. According to certain embodiments, the composition is applied by drenching. According to certain embodiments, the bi-composition is applied by spraying. According to certain embodiments, the composition is applied by dropping.

Suitably, the carrier is a liquid carrier, and more particularly an aqueous carrier, and the member of the aegerolysin family and the member of the MACPF superfamily are dissolved therein. Suitable carriers are well known to the skilled person. A suitable aqueous carrier may for example be a buffer solution, and more particularly a physiological buffer solution. Suitable buffer systems are well known to the skilled person and include as non-limiting examples Tris, TABS, Bicine, Tricine, HEPES, TES, MOPS and PIPES. The pH of the buffer solution is usually in the range of about 6.5 to about 9, such as in the range from about 7.5 to about 8.5, such as about 8. The buffer solution may comprise further additives such as NaCl and/or glycerol. A non-limiting example of a buffer solution useful according to the present invention is a buffer solution comprising 20-50 mM Tris, 0-200 mM NaCl and 0-1% glycerol in deionized water. A more specific non-limiting example of a buffer solution useful according to the present invention is 20 mM Tris, 0.5% glycerol, pH 8.0, in deionized water.

The concentration of the member of the aegerolysin family used may generally be in the range of 0.1 µM to about 1 mM, such as from about 0.5 µM to about 1 mM, about 1 µM to about 1 mM, about 10 µM to about 1 mM, about 50 µM to about 1 mM, about 100 µM to about 1 mM, or about 500 µM to about 1 mM, about 0.1 µM to 500 µM, 0.5 µM to about 500 µM, about 1 µM to about 500 µM, about 10 µM to about 500 µM, about 50 µM to about 500 µM, about 100 µM to about 500 µM, 0.5 µM to about 100 µM, about 1 µM to about 100 µM, about 10 µM to about 100 µM, or about 50 µM to about 100 µM. The member of the MACPF superfamily is used in appropriate amounts to obtain the desired molar ratio in the range from about 3:1 to about 1000:1.

The molar ratio between a member of the aegerolysin family and a member of the MACPF superfamily may generally be in the range from about 3:1 to about 1000:1, such as about 5:1, about 10:1, about 20:1, about 25:1, about 30:1, about 40:1, about 50:1, about 60:1, about 70:1, about 80:1, about 90:1, about 100:1, about 200:1, about 300:1, about 400:1, about 500:1, about 600:1, about 700:1, about 800:1, about 900:1, or about 1000:1.

According to certain embodiments, the molar ratio between a member of the aegerolysin family and a member of the MACPF superfamily is in the range from about 3:1 to about 1000:1. According to some embodiments, the molar ratio between a member of the aegerolysin family and a member of the MACPF superfamily is about 3:1. According to some embodiments, the molar ratio between a member of the aegerolysin family and a member of the MACPF superfamily is about 5:1. According to some embodiments, the molar ratio between a member of the aegerolysin family and a member of the MACPF superfamily is about 10:1. According to some embodiments, the molar ratio between a member of the aegerolysin family and a member of the MACPF superfamily is about 20:1. According to some embodiments, the molar ratio between a member of the aegerolysin family and a member of the MACPF superfamily is about 25:1. According to some embodiments, the molar ratio between a member of the aegerolysin family and a member of the MACPF superfamily is about 30:1. According to some embodiments, the molar ratio between a member of the aegerolysin family and a member of the MACPF superfamily is about 40:1. According to some embodiments, the molar ratio between a member of the aegerolysin family and a member of the MACPF superfamily is about 50:1. According to some embodiments, the molar ratio between a member of the aegerolysin family and a member of the MACPF superfamily is about 60:1. According to some embodiments, the molar ratio between a member of the aegerolysin family and a member of the MACPF superfamily is about 70:1. According to some embodiments, the molar ratio between a member of the aegerolysin family and a member of the MACPF superfamily is about 80:1. According to some embodiments, the molar ratio between a member of the aegerolysin family and a member of the MACPF superfamily is about 90:1. According to some embodiments, the molar ratio between a member of the aegerolysin family and a member of the MACPF superfamily is about 100:1. According to some embodiments, the molar ratio between a member of the aegerolysin family and a member of the MACPF superfamily is about 200:1. According to some embodiments, the molar ratio between a member of the aegerolysin family and a member of the MACPF superfamily is about 300:1. According to some embodiments, the molar ratio between a member of the aegerolysin family and a member of the MACPF superfamily is about 400:1. According to some embodiments, the molar ratio between a member of the aegerolysin family and a member of the MACPF superfamily is about 500:1. According to some embodiments, the molar ratio between a member of the aegerolysin family and a member of the MACPF superfamily is about 600:1. According to some embodiments, the molar ratio between a member of the aegerolysin family and a member of the MACPF superfamily is about 700:1. According to some embodiments, the molar ratio between a member of the aegerolysin family and a member of the MACPF superfamily is about 800:1. According to some embodiments, the molar ratio between a member of the aegerolysin family and a member of the MACPF superfamily is about 900:1. According to some embodiments, the molar ratio between a member of the aegerolysin family and a member of the MACPF superfamily is about 1000:1.

The composition may be applied at least once a week. For example, it may be applied 1 to 3 times a week, such as two times a week. The bi-component protein complex may be applied at least once a day. For example, it may be applied 1 to 3 times a day, such as twice a day.

The present invention also provides the use of a bi-component protein complex or a composition as described herein for the preparation of plant protection agent.

It is understood that all details provided herein with respect to the bi-component protein complex, particularly with respect to the member of the aegerolysin family and the member of the MACPF superfamily, and plant pest, including all embodiments, apply mutatis mutandis to the use for preparation of a plant protection agent.

The present invention also provides a transgenic plant or progeny thereof which expresses or is capable of expressing a bi-component protein complex as described herein.

It is understood that all details provided herein with respect to the bi-component protein complexes, particularly with respect to the member of the aegerolysin family and the member of the MACPF superfamily, including all embodiments, apply mutatis mutandis to the transgenic plant.

A transgenic plant or progeny thereof of the present invention suitably comprises (such as stably transformed with) one or more recombinant nucleic acid molecules (such as DNA) comprising nucleotide sequences that encode a bi-component protein complex as described herein, said nucleotide sequences being operably linked to at least one promoter that is functional in said plant cell to cause the production of mRNA molecules. The transgenic plant or progeny thereof may, for example, comprise one or more recombinant nucleic acid molecules (such as DNA) comprising a nucleotide sequence encoding the member of the aegerolysin family, and one or more recombinant nucleic acid molecules comprising a nucleotide sequence encoding the member of the MACPF superfamily, said nucleotide sequences being operably linked to at least one promoter that is functional in said plant cell to cause the production of mRNA molecules. The coding sequences may be comprised by the same or different recombinant nucleic acid molecules. Hence, the resulting mRNAs may be mono- or polycistronic.

The one or more recombinant nucleic acid molecules may be episomal (not contained within a chromosome) or may be stably integrated into a chromosome of the plant genome. According to certain embodiments, the one or more recombinant nucleic acid molecules may be episomal, such as in the form of a vector (such as in the form of an expression vector). According to certain embodiments, the one or more recombinant nucleic acid molecules are stably integrated into a chromosome of the plant genome.

Promoters useful in accordance with the invention are any known promoters that are functional in a plant cell to cause the production of an mRNA molecule. Many such promoters are known to the skilled person. The use of promoters for protein expression is generally known to those of skilled in the art of molecular biology, for example, see Sambrook et al., Molecular cloning: A Laboratory Manual, Cold Spring Harbor Laboratory, Cold Spring Harbor, N.Y., 1989. The promoter employed may be inducible or constitutive.

Non-limiting examples of plant functional promoters are the *Lactuca sativa* psbA promoter, the tobacco psbA promoter, the tobacco rrn16 PEP+NEP promoter, the CaMV 35S promoter, the 19S promoter, the tomato E8 promoter, the nos promoter, the Mac promoter, the pet E promoter or the ACT1 promoter.

The recombinant nucleic acid molecule(s) may further comprise at least one regulatory element selected from the group consisting of a 5' untranslated region (5' UTR), 3' untranslated region (3' UTR), and transit peptide region.

According to certain embodiments, the recombinant nucleic acid molecule is stably integrated into the genome of the transgenic plant or progeny thereof.

The transgenic plant may be (or derived from) any plant of interest. The transgenic plant may be an angiosperm or a gymnosperm. According to certain embodiments, the transgenic plant is an angiosperm. According to certain embodiments, the transgenic plant is a gymnosperm.

The transgenic plant may be a dicot or monocot. According to certain embodiments, the plant is a dicot. According to certain embodiment, the plant is a monocot.

The transgenic plant may be a food plant (i.e. a plant some parts of which provides food for animal or human consumption), such as fruit plant.

The transgenic plant may be a crop plant, such as a food crop plant. According to certain embodiments, the transgenic plant is a food crop plant such as a potato plant or maize plant. According to some embodiments, the transgenic plant is a potato plant, such as *Solanum tuberosum*. According to some embodiments, the plant is a maize plant. According to some embodiments, the plant is cabbage. According to some embodiments, the plant is asparagus.

CERTAIN DEFINITIONS

As used herein, >>controlling a plant pest<< or >>plant pest control<< means reducing or eliminating the plant pest, such as the pest insect.

As used herein, a "pesticide" is a compound or composition used for reducing or eliminating insects harmful to cultivated plants.

As used herein, "vector" refers to a nucleic acid molecule capable of transporting another nucleic acid molecule to which it has been linked. One type of vector is a "plasmid", which refers to a circular double stranded nucleic acid loop into which additional nucleic acid segments can be ligated. Certain vectors are capable of directing the expression of genes to which they are operatively linked. Such vectors are referred to herein as "expression vectors". Certain other vectors are capable of facilitating the insertion of a recombinant DNA molecule into a genome of a plant. Such vectors are referred to herein as "transformation vectors". In general, vectors of utility in recombinant nucleic acid techniques are often in the form of plasmids. In the present specification, "plasmid" and "vector" can be used interchangeably as the plasmid is the most commonly used form of a vector. Large numbers of suitable vectors are known to those of skill in the art and commercially available.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A "promoter functional in a plant cell" refers to a "promoter" which is capable of supporting the initiation of transcription in plant cells, enabling the synthesis of an mRNA molecule.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. A promoter sequence is "operably-linked" to a gene when it is in sufficient proximity to the transcription start site of a gene to regulate transcription of the gene.

"% sequence identity" of an amino acid sequence to a reference amino acid sequence, as used herein, defines the % identity calculated from the two amino acid sequences as follows: The sequences are aligned using Version 9 of the Genetic Computing Group's GAP (global alignment program), using the default BLOSUM62 matrix with a gap open penalty of −12 (for the first null of a gap) and a gap extension penalty of −4 (for each additional null in the gap). After alignment, % identity is calculated by expressing the number of matches as a percentage of the number of amino acids in the reference amino acid sequence.

Where a numerical limit or range is stated herein, the endpoints are included. Also, all values and sub ranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Biological Assays
I. Feeding Bioassay with Potato Leaves Treated with Recombinant Proteins from the Fungal Genus *Pleurotus* to Assess Toxicity to CPB
1. Principle:

This bioassay was used to assess the impact of recombinant proteins from fungal genus *Pleurotus* on the survival of CPB larvae. We used potato leaves treated with recombinant proteins. The bioassay was carried out for 5 days. The survival rate was recorded daily. Weight measurements were recorded on day 1 and day 5.

2. Recombinant Proteins:

Proteins from the fungal genus *Pleurotus*, OlyA6, PlyA2, EryA and PlyB, were prepared in recombinant form by the use of heterologous expression system for protein production in *Escherichia coli*. Proteins were purified with chromatographic procedures and stored in buffer solutions at −20° C. Appropriate working protein mixtures, containing an aegerolysin and its protein partner, were prepared. The concentrations of fungal aegerolysin and PlyB were 0.5 mg/mL and 0.04 mg/mL, respectively.

3. Insects:

CPB larvae, collected from potato fields a day prior to the experiments, were divided into two groups: young larvae (L1+L2) and old larvae (L3+L4). In L1 and L2, the pronotum is entirely black. In L3, the anterior margin of the pronotum appears orange-brown. In L4, about half the pronotum is light brown anteriorly.

4. Procedure:

Potato leaf disks, 14 mm in diameter, were soaked in 5 mL of each protein mixture for 5 min, before being placed in 6-well microplate. A single CPB larva was transferred to each well (FIG. 3). Fresh potato disk leaves, treated with proteins, were added every second day. Three replicate 6-well plates per treatment were performed, and the experiment repeated twice independently, giving a total of 36 larvae for each treatment. The bioassay was performed in an incubator at 22° C.±1, RH 70% and a photoperiod of 16:8 (L:D). Buffer (20 mM Tris 0.5% glycerol pH 8.0) treated leaf disks were used as a negative control and insecticide Actara 25 WG (a.i. thiametoxam) treated leaf disks as a positive control. The time-based larval mortality was analyzed by Kaplan-Meier survival analysis and the effect of protein mixtures on larval weight change by Kruskal-Wallis test, followed by Dunn's post hoc test.

II. Feeding Bioassay with Artificial Diet for Adult WCR Mixed with Recombinant Proteins from the Fungal Genus *Pleurotus* to Assess Toxicity to WCR 1. Principle This bioassay was used to assess the impact of recombinant proteins from fungal genus *Pleurotus* on the survival of WCR beetles. We used artificial diet mixed with recombinant proteins. The bioassay was carried out for 7 days. The survival rate was recorded daily.

2. Recombinant Proteins

Proteins from the fungal genus *Pleurotus*, OlyA6, PlyA2, EryA and PlyB, were prepared in recombinant form by the use of heterologous expression system for protein production *Escherichia coli*. Proteins were purified with chromatographic procedures and stored in buffer solutions at −20° C. Appropriate working protein mixtures, containing an aegerolysin and its protein partner, were prepared. The final concentrations of the fungal aegerolysin and PlyB in the mixture with artificial food were 0.5 mg/mL and 0.04 mg/mL, respectively.

3. Insects:

Beetles, used for the experiments, were collected from corn fields a day prior to the experiments.

4. Procedure:

An artificial diet (pH 7.0) comprising of: sucrose (33 g), alphacel (18.6 g), casein (15.9 g), soy flour (12.4 g), wheat germ (12.4 g), brewer's yeast (5 g), vitamin mix (Vanderzant, 1.2 g), salt mix (Wesson, 1.2 g), cholesterol (0.3 g), glycerol (11 mL) and $dH_2O$ (82.5 mL), was mixed for WCR. 30 μL mixture, comprising of artificial diet and protein complexes (15 μl each) was pipetted to each well of a 6-well plate. A WCR adult was placed in each well (FIG. 4). Three replicate 6-well plates per treatment were performed, and the experiment repeated twice independently, giving a total of 36 adult insects for each treatment. The bioassay was performed in an incubator at 22° C.±1, RH 70% and a photoperiod of 16:8 (L:D). Buffer (20 mM Tris 0.5% glycerol pH 8.0) mixed with artificial food (1:1, v:v) was used as a negative control and 0.5% Decis (a.i. deltamethrin) mixture as a positive control.

Biophysical Tests

III. Surface Plasmon Resonance Measurements

1. Principle:

We used surface plasmon resonance for determining interactions of proteins from the fungal genus *Pleurotus* with artificial lipid vesicles containing CPE. We immobilized large unilamellar vesicles (LUV) containing CPE on the surface of the sensor chip. Solutions of the appropriate aegerolysin, alone or in combination with PlyB were injected across the surface of the sensor chip.

2. Reagents:

The interactions were monitored on Biacore X surface plasmon resonance (SPR)-based refractometer, using L1 chip. For immobilisation of LUVs composed of mixture of lipids (CPE: palmitoyl-2-oleoyl-sn-glycero-3-phosphocholine [POPC]:Chol [5:47.5:47.5, mol:mol:mol]) and as running buffer we used 20 mM Tris, 140 mM NaCl, 5 μM EDTA pH 7.4. As analytes we used recombinant proteins from the fungal genus *Pleurotus*: OlyA6, EryA, PlyA2 and PlyB. Experiments were performed at 25° C. The data were processed with BIAevaluation software (GE Healthcare).

3. Procedure:

After initial cleaning of the chip with regeneration solutions (sodium dodecyl sulphate [SDS] and octyl β-D-glucopyranoside [OG], 1-min injection, flow rate 10 μL/min), LUVs containing CPE were bound to the second flow cell of sensor chip L1 to reach response of approximately 7000 RU. The first flow cell was left empty and used to control the possible nonspecific binding of proteins to the dextran matrix. Loosely bound LUVs were washed from the surface with 1-min injection of 100 mM NaOH. The nonspecific binding of the proteins was minimized with 1-minute injection of 0.1 mg/mL bovine serum albumin at flow rate 30 μL/min. Appropriate solutions of proteins and protein complexes were injected at a flow rate 10 μL/min. The interactions of OlyA6, PlyA2 or EryA with LUVs containing CPE were tested. Furthermore, we analysed the interactions of protein complexes OlyA6/PlyB, PlyA2/PlyB or EryA/PlyB with LUVs. Regeneration between injection was achieved with 1-min injection of 0.5% SDS and 40 mM OG with flow rate of 10 μL/min.

IV. Lytic Activity of Fungal Aegerolysins with their Partner PlyB

1. Principle:

We used calcein-loaded small unilamellar vesicles (SUVs) containing CPE in order to confirm the lytic activity of OlyA6, PlyA2 or EryA with their protein partner PlyB.

2. Reagents:

The lytic activity of the protein complexes was assayed in a fluorescence microplate reader at 25° C. We used calcein-loaded SUVs composed of mixture of lipids (CPE:POPC:Chol [5:47.5:47.5, mol:mol:mol]).

3. Procedure:

Protein mixtures comprising fungal aegerolysins OlyA6, PlyA2 or EryA and PlyB (12.5:1, mol:mol) were dispensed into a multi-well microplate at the following concentrations: 10 μg/mL OlyA6, PlyA2 or EryA combined with 0.8 μg/mL PlyB. Calcein-loaded SUVs were added to the protein mixtures (5 μg/mL). The SUVs were excited at 485 nm and the intensity of the emitted fluorescence of released calcein was monitored at 535 nm for 30 min with 20 s intervals. The intensities of the emitted fluorescence at t=0 and t=30 were determined as $F_0$ and F, respectively SUVs were fully lysed with 1 mM Triton X-100, and measured fluorescence was determined as maximal fluorescence intensity ($F_{max}$) The percentage of calcein release R (%) was calculated as:

$$R(\%) = \frac{F - Fo}{F\max - Fo} * 100$$

Results

I. CPB Feeding Bioassay with Potato Leaves Treated with Recombinant Proteins from Fungal Genus *Pleurotus*

The effect of bi-component pesticidal complexes, comprising fungal aegerolysin and PlyB on the CPB larvae was tested. Larval mortality and body weight were analyzed. Exposure of CPB larvae to leaf disks treated with OlyA6/PlyB or PlyA2/PlyB protein mixtures caused significant larval mortality on day 5 after initiation of feeding in both groups (FIGS. 5-6). EryA/PlyB protein mixture caused significant larval mortality also in young larvae (L1+L2). The feeding behavior of exposed larvae was significantly different from that of control larvae (FIGS. 5-6). After day 1, exposed larvae showed decrease in food consumption. L1+L2 treated with EryA/PlyB showed a significantly lower weight increase compared with the weights of control larvae, whereas all protein mixtures significantly reduced larval weight increase in the case of L3+L4. Individual aegerolysins (OlyA6, PlyA2 or EryA) or only the component B (PlyB) alone did not show a significant effect on larval weight change in L1+L2 or L3+L4.

Figure 7:
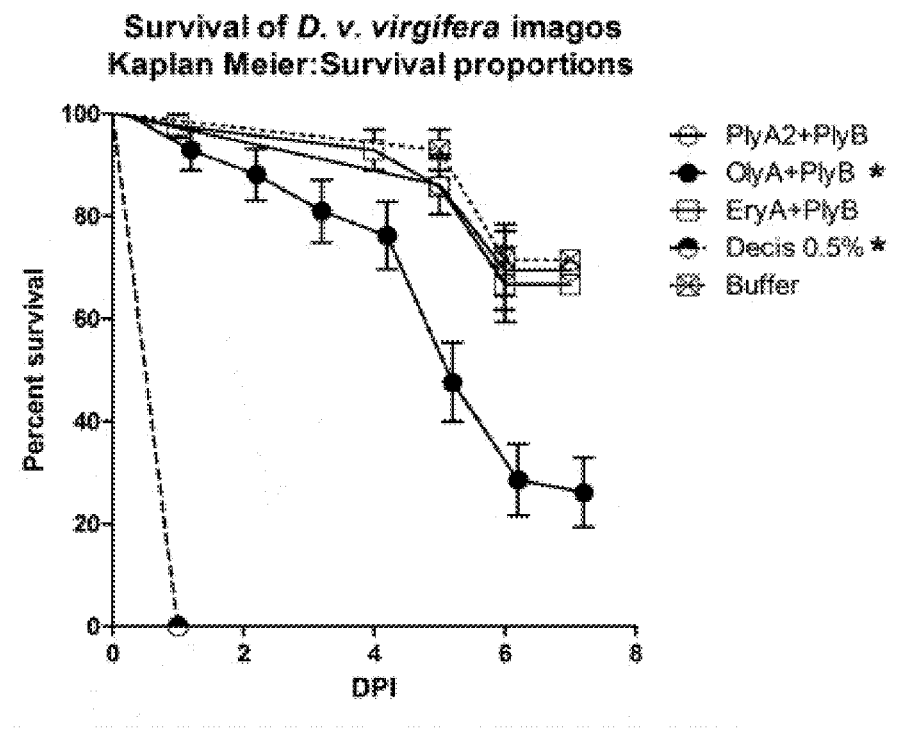

II. Feeding Bioassay with Artificial Diet Mixed with Recombinant Proteins from Fungal Genus *Pleurotus* Targeting Adult WCR The effect of bi-component pesticidal complexes, comprising fungal aegerolysin and PlyB on the WCR beetles was tested. Insect mortality was evaluated on a daily basis. Exposure of WCR to artificial food mixed with OlyA6/PlyB resulted in significant increase in mortality on day 5 after the initiation of feeding. The feeding behaviour of exposed larvae was different from that of control larvae. After day 4, exposed larvae showed decrease in food consumption (FIG. 7).

III. Surface Plasmon Resonance Measurements

We monitored the binding of fungal aegerolysins OlyA6, PlyA2 or EryA (with or without pleurotolysin B) to large unilamellar vesicles containing CPE using surface plasmon resonance. The results show clearly that all tested aegerolysins specifically interact with CPE-containing artificial membranes, and that this interaction is stabilized in the presence of PlyB (FIG. 8).

IV. Lytic Activity of Fungal Aegerolysins with their Partner PlyB

The results show that artificial membranes were permeabilized with aegerolysins OlyA6, PlyA2 or EryA in combination with PlyB, if the membranes contained CPE. Protein complexes OlyA6/PlyB and PlyA2/PlyB are more lytic than EryA/PlyB (FIG. 9).

REFERENCES

Alyokhin, A., Baker, M., Mota-Sanchez, D., Dively, G., Grafius, E. (2008). Colorado Potato Beetle Resistance to Insecticides. American Journal Of Potato Research, 85(6), 395-413. http://dx.doi.org/10.1007/s12230-008-9052-0

Alyokhin, A., Mota-Sanchez, D., Baker, M., Snyder, W., Menasha, S., Whalon, M. et al. (2014). The Red Queen in a potato field: integrated pest management versus chemical dependency in Colorado potato beetle control. Pest Management Science, 71(3), 343-356. http://dx.doi.org/10.1002/ps.3826

Anderluh, G., Kisovec, M., Kraševec, N., Gilbert, R. J. (2014). Distribution of MACPF/CDC proteins. Subcellular Biochemistry, 80, 7-30

Berne, S., Lah, L., Sepčić, K. (2009). Aegerolysins: Structure, function, and putative biological role. Protein Science, 18(4), 694-706. http://dx.doi.org/10.1002/pro.85

Bhat, H., Ishitsuka, R., Inaba, T., Murate, M., Abe, M., Makino, A. et al. (2015). Evaluation of aegerolysins as novel tools to detect and visualize ceramide phosphoethanolamine, a major sphingolipid in invertebrates. The FASEB Journal, 29(9), 3920-3934. http://dx.doi.org/10.1096/fj.15-272112

Butala, M., Novak, M., Kraševec, N., Skočaj, M., Veranič P., Maček, P., Sepčić, K. (2017). Aegerolysins: Lipid-binding proteins with versatile functions. Seminars In Cell And Developmental Biology. http://dx.doi.org/10.1016/j.semcdb.2017.05.002

Casagrande, R A. (1987). The colorado Potato Beetle: 125 Years of mismanagement. American Entomologist, 33(3), 142-150. https://doi.org/10.1093/besa/33.3.142

Chu, C., Sun, W., Spencer, J., Pittendrigh, B., Seufferheld, M. (2014). Differential effects of RNAi treatments on field populations of the western corn rootworm. Pesticide Biochemistry And Physiology, 110, 1-6. http://dx.doi.org/10.1016/j.pestbp.2014.02.003

Crone, H. D., Bridges, R G. (1963). The phospholipids of the housefly, *Musca domestica*. Biochemical Journal, 89, 11-21

Devine, G., Furlong, M. (2007). Insecticide use: Contexts and ecological consequences. Agriculture And Human Values, 24(3), 281-306. http://dx.doi.org/10.1007/s10460-007-9067-z Gassmann, A. (2012). Field-evolved resistance to Bt maize by western corn rootworm: Predictions from the laboratory and effects in the field. Journal Of Invertebrate Pathology, 110(3), 287-293. http://dx.doi.org/10.1016/j.jip.2012.04.006

Gassmann, A., Petzold-Maxwell, J., Keweshan, R., Dunbar, M. (2011). Field-Evolved Resistance to Bt Maize by Western Corn Rootworm. Plos ONE, 6(7), e22629. http://dx.doi.org/10.1371/journal.pone.0022629

Itasaka, O., Hori, T., Uno, A., Iwamori, M. (1973). Occurrence of Ceramide Phosphorylethanolamine Containing Hydroxy Fatty Acid in a Bivalve. Journal of Biochemistry, 73, 191-193.

Jakka, S., Shrestha, R., Gassmann, A. (2016). Broad-spectrum resistance to *Bacillus thuringiensis* toxins by western corn rootworm (*Diabrotica virgifera virgifera*). Scientific Reports, 6(1). http://dx.doi.org/10.1038/srep27860

Kaiser-Alexnat, R. (2009). Protease activities in the midgut of Western corn rootworm (*Diabrotica virgifera virgifera* LeConte). Journal Of Invertebrate Pathology, 100(3), 169-174. http://dx.doi.org/10.1016/j.jip.2009.01.003

Kelker, M., Berry, C., Evans, S., Pai, R., McCaskill, D., Wang, N. et al. (2014). Structural and Biophysical Characterization of *Bacillus thuringiensis* Insecticidal Proteins Cry34Ab1 and Cry35Ab1. Plos ONE, 9(11), e112555. http://dx.doi.org/10.1371/journal.pone.0112555

Kuhlmann, U., Burgt, W. A. C. M., 1998. Possibilities for biological control of the western corn rootworm, *Diabrotica virgifera virgifera* LeConte, in Central Europe. Biocontrol News And Information, 19, 59-68

Ludwick, D., Meihls, L., Ostlie, K., Potter, B., French, L., Hibbard, B. (2017). Minnesota field population of western corn rootworm (Coleoptera: Chrysomelidae) shows incomplete resistance to Cry34Ab1/Cry35Ab1 and Cry3Bb1. Journal Of Applied Entomology, 141(1-2), 28-40. http://dx.doi.org/10.1111/jen.12377

Lukoyanova, N., Kondos, S. C., Farabella, I., Law, R. H. P., Reboul, C. F., Caradoc-Davies, T. T., Spicer, B., Kleifeld, O., Traore, D. A. K., Ekkel, S. M., Voskoboinik, I., Trapani, J. A., Hatfaludi, T. Z., Oliver, K., Hotze, E. M., Tweten, R. K., Whisstock, J. C., Topf, M., Saibil, H. R., Dunstone, M. A. (2015). Conformational changes during pore formation by the perforin-related protein pleurotolysin, PLos Biology, 13 (2), 1-15. http://dx.doi.org/10.1371/journal.pbio.1002049

Masson, L., Schwab, G., Mazza, A., Brousseau, R., Potvin, L., Schwartz, J. (2004). A Novel *Bacillus thuringiensis* (PS14961) Containing a Cry34Ab1/Cry35Ab1 Binary Toxin Specific for the Western Corn Rootworm *Diabrotica virgifera virgifera* LeConte Forms Ion Channels in Lipid Membranes. Biochemistry, 43(38), 12349-12357. http://dx.doi.org/10.1021/bi048946z Meinke, L. J., Siegfried, B. D., Wright, R. J., Chandler, L. D. (1998). Adult Susceptibility of Nebraska Western Corn Rootworm (Coleoptera: Chrysomelidae) Populations to Selected Insecticides. Journal of Economic Entomology, 91(3), 594-600

Meissle, M., Pilz, C., Romeis, J. (2009). Susceptibility of *Diabrotica virgifera virgifera* (Coleoptera: Chrysomelidae) to the Entomopathogenic Fungus *Metarhizium anisopliae* when Feeding on *Bacillus thuringiensis* Cry3Bb1-Expressing Maize. Applied And Environmental Microbiology, 75(12), 3937-3943. http://dx.doi.org/10.1128/aem.00432-09

Novak, M., Kraševec, N., Skočaj, M., Maček, P., Anderluh, G., Sepčić, K. (2014). Fungal aegerolysin-like proteins: distribution, activities, and applications. Applied Microbiology And Biotechnology, 99(2), 601-610. http://dx.doi.org/10.1007/s00253-014-6239-9

Ota, K., Leonardi, A., Mikelj, M., Skočaj, M., Wohlschlager, T., Künzler, M. et al. (2013). Membrane cholesterol and sphingomyelin, and ostreolysin A are obligatory for pore-formation by a MACPF/CDC-like pore-forming protein, pleurotolysin B. Biochimie, 95(10), 1855-1864. http://dx.doi.org/10.1016/j.biochi.2013.06.012

Ota, K., Butala, M., Viero, G., Dalla Serra, M., Sepčić, K., Maček, P. (2014). Fungal MACPF-like proteins and aegerolysins: bi-component pore-forming proteins? Subcellular Biochemistry, 80, 271-91.

Pereira, A., Wang, H., Zukoff, S., Meinke, L., French, B., Siegfried, B. (2015). Evidence of Field-Evolved Resistance to Bifenthrin in Western Corn Rootworm (*Diabrotica virgifera virgifera* LeConte) Populations in Western Nebraska and Kansas. PlosS ONE, 10(11), e0142299. http://dx.doi.org/10.1371/journal.pone.0142299

Perlak, F. J., Stone, B. T., Muskopf, Y. M., Petersen, L. J., Parker, G. B., McPherson, S. A., Wyman, J., Love, S., Reed, G., Biever, D., Fischohoff. (1993). Genetically improved potatoes: protection from damage by Colorado potato beetles. Plant Molecular Biology, 22(2), 313-321

Qureshi, N., Chawla, S., Likitvivatanavong, S., Lee, H., Gill, S. (2014). The Cry Toxin Operon of *Clostridium bifermentans* subsp. *malaysia* Is Highly Toxic to *Aedes* Larval Mosquitoes. Applied And Environmental Microbiology, 80(18), 5689-5697. http://dx.doi.org/10.1128/aem.01139-14

Sambrook, J., Fritsch, F. E., and Maniatis, T. (1989) Molecular cloning: A Laboratory Manual. Second edition. New York: Cold Spring Harbor Laboratory Press.

Sepčić, K., Berne, S., Rebolj, K., Batista, U., Plennenitaš, A., Šentjurc, M., Maček, P. (2004). Ostreolysin, a pore-forming protein from the oyster mushroom, interacts specifically with membrane cholesterol-rich lipid domains. FEBS Letters, 575(1-3), 81-85. http://dx.doi.org/10.1016/j.febslet.2004.07.093

Shibata, T., Kudou, M., Hoshi, Y., Kudo, A., Nanashima, N., Miyairi, K. (2010). Isolation and characterization of a novel two-component hemolysin, erylysin A and B, from an edible mushroom, *Pleurotus eryngii*. Toxicon, 56(8), 1436-1442. http://dx.doi.org/10.1016/j.toxicon.2010.08.010

Skočaj, M., Resnik, N., Grundner, M., Ota, K., Rojko, N., Hodnik., V. et al. (2014). Tracking Cholesterol/Sphingomyelin-Rich Membrane Domains with the Ostreolysin A-mCherry Protein. Plos ONE, 9(3), e92783. http://dx.doi.org/10.1371/journal.pone.0092783

Tomita, T., Noguchi, K., Mimuro, H., Ukaji, F., Ito, K., Sugawara-Tomita, N., Hashimoto, Y. (2004). Pleurotolysin, a Novel Sphingomyelin-specific Two-component Cytolysin from the Edible Mushroom *Pleurotus ostreatus*, Assembles into a Transmembrane Pore Complex. Journal Of Biological Chemistry, 279(26), 26975-26982. http://dx.doi.org/10.1074/jbc.m402676200

Tu, J., Zhang, G., Datta, K., Xu C., He, Y., Zhang, Q., Khush, S., Datta, S. K. (2000). Field performance of transgenic elite commercial hybrid rice expressing *Bacillus thuringiensis* δ-endotoxin. Nature, 18, 1101-1104. http://dx.doi.org/10.1038/80310

Vacaru, A. M., van den Dikkenberg, J., Terne, s P., Holthuis, J. C. (2013). Ceramide phosphoethanolamine biosynthesis in *Drosophila* is mediated by a unique ethanolamine phosphotransferase in the Golgi lumen. The Journal of Biological Chemistry, 288(16), 11520-30. http://dx.doi.org/10.1074/jbc.M113.460972

Yalpani, N., Altier, D., Barry, J., Kassa, A., Nowatzki, T., Sethi, A. et al. (2017). An *Alcaligenes* strain emulates *Bacillus thuringiensis* producing a binary protein that kills corn rootworm through a mechanism similar to Cry34Ab1/Cry35Ab1. Scientific Reports, 7(1). http://dx.doi.org/10.1038/s41598-017-03544-9

The invention claimed is:

1. A method for protecting a plant against a plant pest and/or controlling or treating a plant pest, comprising the step of: applying a composition comprising a plurality of molecules selected from the group consisting of ostreolysin and pleurotolysin A, a plurality of molecules of pleurotolysin B (PlyB) and a suitable carrier to said plant;
wherein the ostreolysin is a polypeptide comprising an amino acid sequence having at least 95% sequence identity with SEQ ID NO: 1;
wherein the pleurotolysin A is a polypeptide comprising an amino acid sequence having at least 95% sequence identity with SEQ ID NO: 2
wherein pleurotolysin B is a polypeptide comprising an amino acid sequence having at least 95% sequence identity with SEQ ID NO: 4;
wherein the plant pest is an insect of the family Chrysomelidae; and
wherein the applying the composition is performed by a method selected from spraying, dropping, and drenching.

2. The method according to claim 1, wherein the member of the aegerolysin family is ostreolysin.

3. The method according to claim 1, wherein the ostreolysin is a polypeptide comprising the amino acid sequence of SEQ ID NO: 1.

4. The method according to claim 1, wherein the member of the aegerolysin family is pleurotolysin A.

5. The method according to claim 1, wherein the pleurotolysin A is a polypeptide comprising the amino acid sequence of SEQ ID NO: 2.

6. The method according to claim 1, wherein pleurotolysin B is a polypeptide comprising the amino acid sequence of SEQ ID NO: 4.

7. The method according to claim 1, wherein the insect is a herbivorous insect.

8. The method according to claim 1, wherein the plant pest is a larva of the insect.

9. The method according to claim 1, wherein the plant pest is an imago of the insect.

10. The method according to claim 1, wherein the insect is of the genus *Leptinotarsa*.

11. The method according to claim 1, wherein the insect is *Leptinotarsa decemlineata* (Colorado potato beetle).

12. The method according to claim 1, wherein the insect is of the genus *Diabrotica*.

13. The method according to claim 1, wherein the insect is *Diabrotica virgifera virgifera* (Western corn rootworm).

14. The method according to claim 1, wherein the insect is selected from the group consisting *Leptinotarsa decemlineata* (Colorado potato beetle) and *Diabrotica virgifera virgifera* (Western corn rootworm).

15. The method according to claim 1, wherein the plant pest is Colorado potato beetle larvae.

16. The method according to claim 1, wherein the plant is a crop plant.

17. The method according to claim 1, wherein the plant is a potato plant or maize plant.

18. The method according to claim 1, wherein the plant is a potato plant.

19. The method according to claim 1, wherein the plant is a maize plant.

20. The method according to claim 1, wherein the carrier comprises a buffer solution.

21. The method according to claim 1, wherein the suitable carrier includes one or more of Tris, TABS, Bicine, Tricine, HEPES, TES, MOPS and PIPES.

* * * * *

SEQUENCE LISTING

<160> NUMBER OF SEQ ID NOS: 5

<210> SEQ ID NO 1
<211> LENGTH: 138
<212> TYPE: PRT
<213> ORGANISM: Pleurotus ostreatus

<400> SEQUENCE: 1

```
Met Ala Tyr Ala Gln Trp Val Ile Ile Ile His Asn Val Gly Ser
1               5                   10                  15

Gln Asp Val Lys Ile Lys Asn Leu Lys Ala Ser Trp Gly Lys Leu His
                20                  25                  30

Ala Asp Gly Asp Lys Asp Ala Glu Val Ser Ala Ser Asn Tyr Glu Gly
            35                  40                  45

Lys Ile Val Lys Pro Asp Glu Lys Leu Gln Ile Asn Ala Cys Gly Arg
        50                  55                  60

Ser Asp Ala Ala Glu Gly Thr Thr Gly Thr Phe Asp Leu Val Asp Pro
```

```
                    65                  70                  75                  80
Ala Asp Gly Asp Lys Gln Val Arg His Phe Tyr Trp Asp Cys Pro Trp
                    85                  90                  95

Gly Ser Lys Thr Asn Thr Trp Thr Val Ser Gly Ser Asn Thr Lys Trp
                    100                 105                 110

Met Ile Glu Tyr Ser Gly Gln Asn Leu Asp Ser Gly Ala Leu Gly Thr
                    115                 120                 125

Ile Thr Val Asp Thr Leu Lys Lys Gly Asn
                    130                 135

<210> SEQ ID NO 2
<211> LENGTH: 138
<212> TYPE: PRT
<213> ORGANISM: Pleurotus eryngii

<400> SEQUENCE: 2

Met Ala Tyr Ala Gln Trp Val Ile Ile Ile His Asn Val Gly Ser
1                   5                   10                  15

Lys Asp Val Lys Ile Val Asn Leu Lys Pro Ser Trp Gly Lys Leu His
                    20                  25                  30

Ala Asp Gly Asp Lys Asp Thr Glu Val Ser Ala Ser Lys Tyr Glu Gly
                    35                  40                  45

Thr Val Ile Lys Pro Asp Glu Lys Leu Gln Ile Asn Ala Cys Gly Arg
                    50                  55                  60

Ser Asp Ala Ala Glu Gly Thr Thr Gly Thr Phe Asp Leu Val Asp Pro
65                  70                  75                  80

Ala Asp Gly Asp Lys Gln Val Arg His Phe Tyr Trp Asp Cys Pro Trp
                    85                  90                  95

Gly Ser Lys Ala Asn Thr Trp Thr Val Ser Gly Ser Asn Thr Lys Trp
                    100                 105                 110

Met Ile Glu Tyr Ser Gly Gln Asn Leu Asp Ser Gly Ala Leu Gly Thr
                    115                 120                 125

Ile Thr Val Asp Thr Leu Lys Lys Gly Asn
                    130                 135

<210> SEQ ID NO 3
<211> LENGTH: 138
<212> TYPE: PRT
<213> ORGANISM: Pleurotus eryngii

<400> SEQUENCE: 3

Met Ala Tyr Ala Gln Trp Val Ile Ile Leu Ile His Asn Val Gly Gln
1                   5                   10                  15

Gln Asn Val Lys Ile Lys Asn Leu Asn Ala Ser Trp Gly Lys Leu Tyr
                    20                  25                  30

Ala Asp Gly Asp Lys Asp Thr Glu Val Pro Ala Ser Lys Tyr Glu Gly
                    35                  40                  45

Met Val Ile Ala Pro Asp Gln Val Gln Ile Asn Ala Cys Gly Arg
                    50                  55                  60

Glu Asp Ala Ala Glu Gly Thr Thr Gly Thr Phe Asp Leu Val Asp Pro
65                  70                  75                  80

Asn Asp Ser Asp Lys Gln Val Arg His Phe Ala Trp Asp Cys Pro Trp
                    85                  90                  95

Gly Thr Lys Ala Asn Ser Trp Val Val Gly Gly Ser Asn Ser Lys Trp
                    100                 105                 110

Met Ile Glu Tyr Thr Gly Gln Asn Leu Asp Ser Gly Ala Leu Gly Thr
```

```
            115                 120                 125
Ile Thr Val Asn Thr Leu Arg Ile Gly Asn
    130                 135
```

<210> SEQ ID NO 4
<211> LENGTH: 523
<212> TYPE: PRT
<213> ORGANISM: Pleurotus ostreatus

<400> SEQUENCE: 4

```
Met Glu Ala Val Leu Ser Arg Gln Ala Thr Ala Glu Ala Ile Gly
1               5                   10                  15

Arg Phe Gln Asp Ser Ser Thr Ser Val Gly Leu Val Ala Gly Ser Pro
                20                  25                  30

Ser Thr Arg Ile Arg Arg Gln Ala Asp Asn Val Val Leu Lys Ser Thr
            35                  40                  45

Ser Gln Ala Gly Asp Thr Leu Asn Asp Val Ile Gln Asp Pro Thr Arg
        50                  55                  60

Arg Asn Lys Leu Ile Asn Asp Asn Asn Leu Leu Lys Gly Ile Ile Met
65                  70                  75                  80

Gly Arg Asp Gly Pro Val Pro Ser Ser Arg Glu Leu Ile Val Arg Pro
                85                  90                  95

Asp Thr Leu Arg Ala Ile Ile Asn Asn Arg Ala Thr Ile Glu Thr Thr
                100                 105                 110

Thr Met Glu Ala Glu Phe Thr Glu Thr Leu Met Glu Ser Asn Tyr Asn
            115                 120                 125

Ser Ala Ser Val Lys Val Ser Ala Pro Phe Ile Thr Ala Asn Ser Glu
        130                 135                 140

Tyr Ser Glu Ser Ser Ser Phe Lys Asn Thr Glu Thr Glu Lys Ser Met
145                 150                 155                 160

Tyr Thr Ser Ser Arg Tyr Leu Phe Pro Gln Gly Arg Ile Asp Phe Thr
                165                 170                 175

Thr Pro Asp Ser Gly Phe Asp Asp Val Ile Lys Leu Ser Pro Gln Phe
                180                 185                 190

Thr Ser Gly Val Gln Ala Ala Leu Ala Lys Ala Thr Gly Thr Glu Lys
            195                 200                 205

Arg Glu Ala Leu Gln Asn Leu Phe Gln Glu Tyr Gly His Val Phe Arg
        210                 215                 220

Thr Lys Val His Ile Gly Gly Val Leu Ser Ala His Thr Met Glu Thr
225                 230                 235                 240

Phe Ser Arg Ser Glu Asn Glu Thr Glu Val Lys Gln Asp Val Lys Ala
                245                 250                 255

Gly Leu Glu Gly Ala Val Lys Gly Trp Gly Gly Ala Thr Ala Gly
                260                 265                 270

His Gly Asn Thr Gln Gly Thr Ile Thr Thr Ser Gln Asn Arg Lys Leu
            275                 280                 285

Asn Val Lys Tyr Ile Val Asn Gly Gly Asp Tyr Thr Lys Ile Gln Asn
        290                 295                 300

Thr Glu Glu Trp Val Ala Ser Thr Asn Gln Ser Glu His Trp Arg Val
305                 310                 315                 320

Ile Glu Val Thr Glu Val Thr Ala Val Ala Asp Leu Leu Pro Gln Pro
                325                 330                 335

Ile Arg Gly Gln Val Lys Asp Leu Leu Lys Pro Leu Leu Gly Lys Trp
                340                 345                 350
```

-continued

```
Val Asp Val Glu Lys Val Pro Gly Leu Glu Ser Leu Pro Val Ser Val
        355                 360                 365

Tyr Arg Pro Lys Gly Ala Ile Pro Ala Gly Trp Phe Trp Leu Gly Asp
    370                 375                 380

Thr Ala Asp Ala Ser Lys Ala Leu Leu Val Lys Pro Thr Leu Pro Ala
385                 390                 395                 400

Arg Ser Gly Arg Asn Pro Ala Leu Thr Ser Leu His Gln Gly Ser Gly
                405                 410                 415

Met Thr Glu Gln Pro Phe Val Asp Leu Pro Gln Tyr Gln Tyr Leu Ser
            420                 425                 430

Thr Tyr Phe Gly Ser Phe Ala His Asp Thr Pro Pro Gly Ser Thr Leu
        435                 440                 445

Arg Gly Leu Arg Pro Asp His Val Leu Pro Gly Arg Tyr Glu Met His
    450                 455                 460

Gly Asp Thr Ile Ser Thr Ala Val Tyr Val Thr Arg Pro Val Asp Val
465                 470                 475                 480

Pro Phe Pro Glu Asp Glu Cys Phe Asp Leu Lys Ser Leu Val Arg Val
                485                 490                 495

Lys Leu Pro Gly Ser Gly Asn Pro Pro Lys Pro Arg Ser Ala Leu Lys
            500                 505                 510

Lys Ser Met Val Leu Phe Asp Ser Gly Glu Lys
        515                 520
```

<210> SEQ ID NO 5
<211> LENGTH: 522
<212> TYPE: PRT
<213> ORGANISM: Pleurotus eryngii

<400> SEQUENCE: 5

```
Met Ala Ala Val Leu Ser Arg Gln Ala Ala Thr Ala Glu Ala Val Glu
1               5                   10                  15

Arg Phe Gln Asp Ser Ser Thr Ser Val Gly Leu Val Ala Gly Ser Pro
            20                  25                  30

Ser Arg Ile Arg Arg Gln Ala Asp Asn Val Val Leu Lys Ser Ile Ser
        35                  40                  45

Gln Ala Gly Asp Thr Leu Asn Asp Val Ile Gln Asp Pro Thr Arg Arg
    50                  55                  60

Asn Lys Leu Ile Asn Asp Asn Leu Leu Lys Gly Ile Ile Met Gly
65                  70                  75                  80

Arg Asp Gly Pro Val Pro Ser Ser Arg Glu Leu Ile Glu Arg Pro Asp
                85                  90                  95

Thr Leu Arg Ala Ile Ile Asn Asn Arg Ala Thr Ile Glu Thr Thr Thr
            100                 105                 110

Val Glu Ala Glu Phe Thr Glu Thr Leu Met Glu Ser Asn Tyr Asn Ser
        115                 120                 125

Ala Ser Val Lys Val Ser Ala Pro Phe Val Thr Ala Asn Ser Glu Tyr
    130                 135                 140

Ser Glu Ser Ser Ser Phe Lys Asn Thr Glu Thr Glu Lys Ser Met Tyr
145                 150                 155                 160

Thr Ser Ser Arg Tyr Leu Phe Pro Gln Gly Arg Ile Asp Phe Thr Met
                165                 170                 175

Pro Asp Ser Gly Phe Asp Asp Val Ile Lys Leu Ser Pro Gln Phe Thr
            180                 185                 190

Ser Gly Val Gln Ala Ala Leu Ala Lys Ala Thr Gly Thr Glu Lys Arg
        195                 200                 205
```

```
Glu Ala Leu Gln Asp Leu Phe Leu Glu Tyr Gly His Val Phe Arg Thr
    210                 215                 220
Lys Val His Ile Gly Gly Val Leu Ser Ala His Thr Met Glu Thr Phe
225                 230                 235                 240
Ser Arg Ser Glu Asn Glu Thr Glu Val Lys Gln Asp Ile Lys Ala Gly
                245                 250                 255
Leu Glu Gly Ala Val Lys Gly Trp Gly Gly Gly Ala Thr Ala Gly His
            260                 265                 270
Gly Asn Thr Gln Gly Thr Ile Thr Thr Ser Gln Asn Arg Lys Leu Asp
                275                 280                 285
Val Lys Tyr Ile Val Asn Gly Gly Asp Tyr Thr Lys Ile Gln Asn Thr
    290                 295                 300
Glu Glu Trp Val Ala Ser Thr Asn Gln Ser Glu His Trp Arg Val Ile
305                 310                 315                 320
Glu Val Thr Glu Val Thr Ala Val Ala Asp Leu Leu Pro Gln Pro Ile
                325                 330                 335
Arg Gly Gln Val Lys Asp Leu Leu Lys Pro Leu Leu Gly Lys Trp Val
                340                 345                 350
Asp Val Glu Lys Val Pro Gly Leu Glu Ser Phe Pro Val Ser Val Tyr
                355                 360                 365
Arg Pro Lys Asp Ala Ile Pro Ala Gly Trp Phe Trp Leu Gly Asp Thr
    370                 375                 380
Ala Asp Ala Ser Lys Ala Leu Leu Val Lys Pro Thr Leu Pro Ala Arg
385                 390                 395                 400
Ser Gly Arg Asn Pro Ala Leu Thr Ser Leu His Glu Ser Ser Gly Met
                405                 410                 415
Thr Glu Gln Pro Phe Val Asp Leu Pro Gln Tyr Gln Tyr Leu Ser Thr
                420                 425                 430
Tyr Phe Gly Ser Phe Ala Tyr Asp Thr Pro Pro Gly Ser Thr Leu Arg
            435                 440                 445
Gly Leu Arg Pro Asp His Ile Leu Pro Gly Arg Tyr Glu Met His Gly
            450                 455                 460
Asp Thr Ile Gly Thr Ala Val Tyr Val Thr Arg Pro Val Asp Val Pro
465                 470                 475                 480
Phe Pro Glu Asp Glu Cys Phe Asp Leu Lys Ser Val Val Arg Val Lys
                485                 490                 495
Leu Pro Gly Ser Gly Asn Pro Pro Lys Pro Arg Trp Ala Leu Lys Lys
                500                 505                 510
Ser Met Val Leu Phe Asp Ser Gly Glu Glu
                515                 520
```